(12) United States Patent
Glimcher et al.

(10) Patent No.: US 6,933,125 B2
(45) Date of Patent: Aug. 23, 2005

(54) HUMAN C-MAF COMPOSITIONS AND METHODS OF USE THEREOF

(75) Inventors: Laurie H. Glimcher, West Newton, MA (US); John Douhan, III, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 194 days.

(21) Appl. No.: 09/879,312

(22) Filed: Jun. 12, 2001

(65) Prior Publication Data

US 2002/0160448 A1 Oct. 31, 2002

Related U.S. Application Data

(60) Division of application No. 09/086,010, filed on May 27, 1998, now Pat. No. 6,274,338, which is a continuation-in-part of application No. 09/030,579, filed on Feb. 24, 1998, now abandoned.

(51) Int. Cl.[7] ................................................. C12P 21/06
(52) U.S. Cl. ........................ 435/9.1; 435/325; 424/93.1; 536/23.1
(58) Field of Search .............................. 536/23.1, 24.1; 424/93.1; 455/320.1, 325

(56) References Cited

FOREIGN PATENT DOCUMENTS

WO        WO 97/39721        10/1997

OTHER PUBLICATIONS

Kataoka et al. Molecular and Cellular Biology, Apr. 1995, vol. 15(4), pp. 2180–2190.*
Hedge et al. Molecular and Cellular Biology, May 1998, vol. 18(5), pp. 2729–2737.*
Hodge et al. Science. Dec. 1996, vol. 13;274(5294), pp. 1903–1905.*
Andrews, N.C. et al. "The ubiquitous subunit of erythroid transcription factor NF–E2 is a small basic–leucine zipper protein related to the v–maf oncogene," PNAS., USA, 90 (1993).
Blank et al. "Human MafG is a functional partner for p45 NF–E2 in activating globin gene expression," Blood 89(11):3925–35.
Chesi, Marta et al. (1998) "Frequent Dysregulation Of The c–maf Proto–Oncogene at 16q23 By Translocation of An Ig Locus In Multiple Myeloma" Blood. 91(12):4457–4463.
Ebert et al. "A Moloney MLV–rat somatotropin fusion gene produces biologically active somatotropin in a transgenic pig," Mol. Endocrinol. 2(3):277–83 (1988).
Fujiwara, K.T. et al. "Two new members of the maf oncogene family, mafK and maff, encode nuclear b–Zip proteins lacking putative trans–activator domain," Oncogene, 8:2371–2380 (1993).
Hammer et al. "Genetic engineering of mammalian embryos," J. Animal Sci. 63(1):269–78 (1986).
Ho, I–Cheng et al. (1996) "The Proto–Oncogene c–maf IS Responsible For Tissue–Specific Expression Of Interleukin–4", Cell, 85(7):973–983.
Igarashi, K. et al. "Activity and Expression of Murine Small Maf Family Protein MafK," The Journal of Biological Chemistry, 270(13):7615–7624 (Mar. 31, 1995).
Kataoka, K. et al. "Small Maf Proteins Heterodimerize with Fos and May Act as Competitive Repressors of the NF–E2 Transcription Factor," Mol. Cell. Biol., 15:2180–90 (1995).
Kataoka, K. et al. "Structure–Function Analysis of the maf Oncogene Product, a Member of the b–zip Protein Family," Journal of Virology, 67(4):2133–2141 (Apr. 1993).
Kataoka, K et al. GenBenk™ Accession No. D28596 for Chicken gene for c–maf proto–oncogene product c–Maf, short from complete cds and long form $1^{st}$ exon.
Kurchner, C. et al. GenBank™ Accession No. S74567 for c–maf=c–Maf protein (proto–oncogene) [mice, BALB/c, cerebellum, mRNA, 2736 nt].
Kurschner, C. et al. "The maf Proto–oncogene Stimulates Transcription from Multiple Sites in a Promoter That Directs Purkinje Neuron–Specific Gene Expression," Mol Cell Biol, 15:246–54 (1995).
Mullins et al. "Transgenesis in the rat and larger mammals," J. Clin. Invest. 97(7):1557–60 (1996).
Swaroop, A. et al. "A conserved retina–specific gene encodes a basic motif/leucine zipper domain", Proc. Natl. Acad. Sci. USA, 89:266–270 (Jan. 1992).
Toki et al. "Human small Maf proteins form heterodimers with CNC family transcription factors and recognize the NF–E2 motif," Oncogene 14:1901–10.
Wall et al. "Transgenic dairy cattle: genetic engineering on a large scale," J. Dairy Sci. 80(9):2213–24 (1996).
Sakai, M. et al. "Rat maf related genes: specific expression in chondrocytes, lens and spinal cord," Oncogene 14:745–50 (1997).

* cited by examiner

Primary Examiner—Joseph Woitach
(74) Attorney, Agent, or Firm—Lahive & Cockfield LLP; Giulio A. DeConti, Jr.; Megan E. Williams

(57) ABSTRACT

Isolated nucleic acid molecules encoding human c-Maf, and isolated c-Maf proteins, are provided. The invention further provides antisense nucleic acid molecules. recombinant expression vectors containing a nucleic acid molecule of the invention, host cells into which the expression vectors have been introduced and non-human transgenic animals carrying a human c-Maf transgene. The invention further provides human c-Maf fusion proteins and anti-human c-Maf antibodies. Methods of using the human c-maf compositions of the invention are also disclosed, including methods for detecting human c-Maf activity in a biological sample, methods of modulating human c-Maf activity in a cell, and methods for identifying agents that modulate the activity of human c-Maf.

25 Claims, 3 Drawing Sheets

```
              ATGGCTTCAGAACTGGCAATGAGCAATTCCGACCTGCCCACCAGTCCCCTGGCCATGGAATATGTTAATG
              10        20        30        40        50        60        70 mouse maf cod ATGGCTTCAGAACTGGCAATGAACAATTCCGACCTGCCCACCAGTCCCCTGGCCATGGAATATGTTAATG
human maf cod ATGGCTTCAGAACTGGCAATGAGCAACTCCGACCTGCCCACCAGTCCCCTGGCCATGGAATATGTTAATG ACTTCGATCTGATGAAGTTTGAAGTGAAAAAGGAACCGGTGGAGACCGACCGCATCATCAGCCAGTGCGG
              80        90        100       110       120       130       140 mouse maf cod ACTTCGATCTGATGAAGTTTGAAGTGAAAAAGGAACCGGTGGAGACCGACCGCATCATCAGCCAGTGCGG
human maf cod ACTTCGATCTGATGAAGTTTGAAGTGAAAAAGGAACCGGTGGAGACCGACCGCATCATCAGCCAGTGCGG CCGTCTCATCGCCGGGGGCTCGCTGTCCTCCACCCCCATGAGCACGCCCTGCAGCTCGGTGCCCCCGTCC
              150       160       170       180       190       200       210 mouse maf cod CCGTCTCATCGCCGGGGGCTCGCTGTCCTCCACCCCCATGAGCACGCCCTGCAGCTCGGTGCCCCCGTCC
human maf cod CCGTCTCATCGCCGGGGGCTCGCTGTCCTCCACCCCCATGAGCACGCCCTGCAGCTCGGTGCCCCCGTCC CCCAGCTTCTCGGCGCCCAGCCCGGGCTCGGGCGGCGAACAGAAGGCGCACCTGGAAGACTACTACTGGA
              220       230       240       250       260       270       280 mouse maf cod CCCAGCTTCTCGGCGCCCAGCCCGGGCTCGGGACCGAACAGAAGGCGCACCTGGAAGACTACTACTGGA
human maf cod CCCAGCTTCTCGGCGCCCAGCCCGGGCTCGGAGGCGAACAGAAGGCGCACCTGGAAGACTACTACTGGA TGACCGGCTACCCGCAGCAGCTGAACCCGGAGGCGCTGGGCTTCAGCCCGGAGGACGCGGTCGAGGCGCT
              290       300       310       320       330       340       350 mouse maf cod TGACCGGCTACCCGCAGCAGCTCAACCCGGAGGCGCTGGGCTTCAGCCCGGAGGACGCGGTCGAGGCGCT
human maf cod TGACCGGCTACCCGCAGCAGCTGAACCCGGAGGCGCTGGGCTTCAGCCCGGAGGACGCGGTCGAGGCGCT CATCAGCAACAGCCACCAGCTCCGGGGTGGCTTCGATGGCTATGCGCGGGGGGCCCACCAGCTGGCCGCG
              360       370       380       390       400       410       420 mouse maf cod CATCAGCAACAGCCACCAGCTCCAGGGTGGCTTCGATGGCTATGCGCGCCGAGCGCAGCAGCTGGCCGCG
human maf cod CATCAGCAACAGCCACCAGCTCCGGGCGGGCTTCGATGGCTATGCGCGCGGGGCGCAGCAGCTAGCCGCG GCGGCGGGGGCCGGTCCCGGCGCCTCCTTGGGCGGCAGCGGCGAGGAGATGGGCCCCGCCGCCGCCGTGG
              430       440       450       460       470       480       490 mouse maf cod GCAGCGGGGGCTGCCGCCGGCGCCTCCCTGGGCGGCAGCGGCGAGGAGATGGGCCCCGCCGCCGCCGTGG
human maf cod GCGGCCGGGGCAGGTGCCGGCGCCTCCTTGGGCGGCAGCGGCGAGGAGATGGGCCCCGCCGCCGCCGTGG TGTCCGCCGTCATCGCCGCGGCCGCCGCGCAGAGCGGCGCGGGCCCGCACTACCATCACCACCACCACCA
              500       510       520       530       540       550       560 mouse maf cod TGTCCGCCGTGATCGCCGCGGCCGCCGCGCAGAGCGGCGCGGCACCCACTACCATCACCACCACCACCA
human maf cod TGTCCGCCGTGATCGCCGCGGCCGCCGCGCAGAGCGGCGCGGGCCGCACTACCACCACCACCACCACCA CGCCGCGGGGCACCACCACCATCCGACGGCCGGCGCGCCGGGCGCCGCGGGCGGCGCGTCTTCTTCTTCG
              570       580       590       600       610       620       630 mouse maf cod CGCCGCGGGCCACCACCACCATCCGACGGCCGGCGCCCGGCAACCGCGGGGGCGCGTCTTCTTCTTCG
human maf cod CGCCGCGGCGCACCACCACCACCGACGGCCGGCGCCGCGGCCCGCGGGCAGCGGCTGCTTTGGCC GGTGGCGCTGGTGGCGCGGGCGGCGGTGGCCCGGCCAGCGTTGGGGGCGGCGGCGGCGGCGGCGGCGGCG
              640       650       660       670       680       690       700 mouse maf cod AACGGCGCGGGTGGCGCGGGCGGCGGTGGCCCGGCCAACCGGGGGCGGCGGCGGCGGCGACGGCGGCG
human maf cod GGTGGCGCTGGGGGCGCGGGCGGCGGTGGCCCGGCCAGCGTTGGGGGCGGCGGCGGCGGCGGCGGCGGCG
```

FIGURE 1A

```
              GGGGCGGGGGGGGGGCGGGGGGCGCCCTTCACCCGCACCATTCCGCGGGCGGCCTGCACTTCGACGACCG
                   710       720       730       740       750       760       770
mouse maf cod  GGGGCAGGGGGGGGCGGGGGGCGCCCTTCACCCGCACCATTCCGCGGGCGGCCTGCACTTCGACGACCG
human maf cod  GAGGCGGGGGGGCGCGGGGGCGCCCTGCACCCGCACCAGCCGCCGGCGGCCTGCACTTCGACGACCG CTTCTCGGACGAGCAGTTGGTGACCATGTCTGTGCGCGACTTGAACCGGCAGCTGCGCGGGGTCAGCAAG
                   780       790       800       810       820       830       840
mouse maf cod  CTTCTCGGACGAGCAGTTGGTGACCATGTCGGTGCGCGAACTGAACCGGCAGCTGCGCGGGGTCAGCAAG
human maf cod  CTTCTCCGACGAGCAGCTGGTGACCATGTCTGTGCGCGACTTGAACCGGCAGCTGCGCGGGGTCAGCAAG GAGGAGGTGATCCGGCTGAAGCAGAAGAGGCGGACCCTGAAAAACCGCGGCTATGCCCAGTCCTGCCGCT
                   850       860       870       880       890       900       910
mouse maf cod  GAGGAGGTGATCCGACTGAAGCAGAAGAGGCGGACCCTGAAAAACCGCGGCTATGCCCAGTCCTGCCGCT
human maf cod  GAGGAGGTGATCCGGCTGAAGCAGAAGAGGCGGACCCTGAAAAACCGCGGCTATGCCAAGTCCTGCCGCT TCAAGAGGGTGCAGCAGAGACACGTCCTGGAGTCGGAGAAGAACCAGCTGCTGCAGCAGGTCGACCACCT
                   920       930       940       950       960       970       980
mouse maf cod  TCAAGAGGGTGCAGCAGAGACACGTCCTGGAGTCGGAGAAGAACCAGCTGCTGCAGCAGGTAGACCACCT
human maf cod  TCAAGAGGGTGCAGCAGAGACACGTCCTGGAGTCGGAGAAGAACCAGCTGCTGCAGCAAGTCGACCACCT CAAGCAGGAGATCTCCAGGCTGGTGCGCGAGAGGGACGCGTACAAGGAGAAATACGAGAAGTTGGTGAGC
                   990      1000      1010      1020      1030      1040      1050
mouse maf cod  CAAGCAGGAGATCTCCAGGCTGGTGCGCGAAAGGGACGCCTACAAGGAGAAATACGAGAAGCTGGTGAGC
human maf cod  CAAGCAGGAGATCTCCAGGCTGGTGCGCGACAGGGACGCCTACAAGGAGAAATACGAGAAGTTGGTGAGC AGCGGCTTCCGAGAAAACGGCTCGAGCAGCGACAACCCTTCCTCTCCCGAGTTTTTCATGTGXXXXXXXX
                  1060      1070      1080      1090      1100      1110      1120
mouse maf cod  AACGGCTTCCGAGAAAACGGCTCGAGCAGCGACAACCCTTCCTCTCCCGAATTTTTCATGTG
human maf cod  AGCGGCTTCCGAGAAAACGGCTCGAGCAGCGACAACCCGTCCTCTCCCGAGTTTTTCATAACTGAGCCCA XXXXXXXXXXXXXXXXXXXXXXXXXXXXXXXXXXXXXXXXXXXXXXXXXXXXXXXXXXXXXXXXXXXXX
                  1130      1140      1150      1160      1170      1180      1190
mouse maf cod
human maf cod  CTCGCAAGTTGGAGCCATCAGTGGGATACGCCACATTTTGGAAGCCCCAGCATCGTGTACTTACCAGTGT XXXXXXXXXXXXX
                  1200
mouse maf cod
human maf cod  GTTCACAAAATGA
```

FIGURE 1B

```
                MASELAMSNSDLPTSPLAMEYVNDFDLMKFEVKKEPVETDRIISQCGRLIAGGSLSSTPMSTPCSSVPPS
                 10        20        30        40        50        60        70
mouse c-maf t   MASELAM NNSDLPTSPLAMEYVNDFDLMKFEVKKEPVETDRIISQCGRLIAGGSLSSTPMSTPCSSVPPS
human c-maf t   MASELAM SNSDLPTSPLAMEYVNDFDLMKFEVKKEPVETDRIISQCGRLIAGGSLSSTPMSTPCSSVPPS PSFSAPSPGSGGEQKAHLEDYYWMTGYPQQLNPEALGFSPEDAVEALISNSHQLQGGFDGYARGAQQLAA
                 80        90       100       110       120       130       140
mouse c-maf t   PSFSAPSPGS GSEQKAHLEDYYWMTGYPQQLNPEALGFSPEDAVEALISNSHQL QGGFDGYARGAQQLAA
human c-maf t   PSFSAPSPGS RGEQKAHLEDYYWMTGYPQQLNPEALGFSPEDAVEALISNSHQL RGGFDGYARGAQQLAA AAGAGAGASLGGSGEEMGPAAAVVSAVIAAAAAQSGAGPHYHHHHHHAAGHHHHPTAGAPGAAGGAAASA
                150       160       170       180       190       200       210
mouse c-maf t   AAGAGAGASLGGSGEEMGPAAAVVSAVIAAAAAQSGA APHYHHHHHHAAGHHHHPTAGAPG TAGGASSS
human c-maf t   AAGAGAGASLGGSGEEMGPAAAVVSAVIAAAAAQSGA GPHYHHHHHHAAGHHHHPTAGAPG AAGGAAASA GGAGGAGGGGPASVGGGGGGGGGGGGGAGGALHPHHAAGGLHFDDRFSDEQLVTMSVRDLNROLRGVSK
                220       230       240       250       260       270       280
mouse c-maf t   NGAGGAGGGGPA NTGCGGGD GGGT AGAG GALHPHH SAGGLHFDDRFSDEQLVTMSVR DL NRQLRGVSK
human c-maf t   GGAGGAGGGGPA SVGGGGG GGGG GGAA GALHPHH AAGGLHFDDRFSDEQLVTMSVR DL NRQLRGVSK EEVIRLKQKRRTLKNRGYAQSCRFKRVQQRHVLESEKNQLLQQVDHLKQEISRLVRERDAYKEKYEKLVS
                290       300       310       320       330       340       350
mouse c-maf t   EEVIRLKQKRRTLKNRGYA QSCRFKRVQQRHVLESEKNQLLQQVDHLKQEISRLVRERDAYKEKYEKLVS
human c-maf t   EEVIRLKQKRRTLKNRGYA KSCRFKRVQQRHVLESEKNQLLQQVDHLKQEISRLVRERDAYKEKYEKLVS SGFRENGSSSDNPSSPEFFITEPTRKLEPSVGYATFWKPQHRVLTSVFTK-
                 360       370       380       390       400
mouse c-maf t   NGFRENGSSSDNPSSPEFFM
human c-maf t   SGFRENGSSSDNPSSPEFFITEPTRKLEPSVGYATFWKPQHRVLTSVFTK.
```

FIGURE 2

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 1203 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 1..1203

(xi) SEQUENCE DESCRIPTION: SEQ ID NO: 1:

```
ATG GCA TCA GAA CTG GCA ATG AGC AAC TCC GAC CTG CCC ACC AGT CCC        48
Met Ala Ser Glu Leu Ala Met Ser Asn Ser Asp Leu Pro Thr Ser Pro
 1               5                  10                  15

CTG GCC ATG GAA TAT GTT AAT GAC TTC GAT CTG ATG AAG TTT GAA GTG        96
Leu Ala Met Glu Tyr Val Asn Asp Phe Asp Leu Met Lys Phe Glu Val
            20                  25                  30

AAA AAG GAA CCG GTG GAG ACC GAC CGC ATC ATC AGC CAG TGC GGC CGT       144
Lys Lys Glu Pro Val Glu Thr Asp Arg Ile Ile Ser Gln Cys Gly Arg
        35                  40                  45

CTC ATC GCC GGG GGC TCG CTG TCC TCC ACC CCC ATG AGC ACG CCC TGC       192
Leu Ile Ala Gly Gly Ser Leu Ser Ser Thr Pro Met Ser Thr Pro Cys
    50                  55                  60

AGC TCG GTG CCC CCG TCC CCC AGC TTC TCG GCG CCC AGC CCG GGC TCG       240
Ser Ser Val Pro Pro Ser Pro Ser Phe Ser Ala Pro Ser Pro Gly Ser
65                  70                  75                  80

CGA GGC GAA CAG AAG GCG CAC CTG GAA GAC TAC TAC TGG ATG ACC GGC       288
Arg Gly Glu Gln Lys Ala His Leu Glu Asp Tyr Tyr Trp Met Thr Gly
                85                  90                  95

TAC CCG CAG CAG CTG AAC CCC GAG GCG CTG GGC TTC AGC CCC GAG GAC       336
Tyr Pro Gln Gln Leu Asn Pro Glu Ala Leu Gly Phe Ser Pro Glu Asp
            100                 105                 110

GCG GTC GAG GCG CTC ATC AGC AAC AGC CAC CAG CTC CGG GGC GGC TTC       384
Ala Val Glu Ala Leu Ile Ser Asn Ser His Gln Leu Arg Gly Gly Phe
        115                 120                 125

GAT GGC TAT GCG CGC GGG GCG CAG CAG CTA GCC GCG GCG GCC GGG GCA       432
Asp Gly Tyr Ala Arg Gly Ala Gln Gln Leu Ala Ala Ala Ala Gly Ala
    130                 135                 140

GGT GCC GGC GCC TCC TTG GGC GGC AGC GGC GAG GAG ATG GGC CCC GCC       480
Gly Ala Gly Ala Ser Leu Gly Gly Ser Gly Glu Glu Met Gly Pro Ala
145                 150                 155                 160
```

| | | |
|---|---|---|
| GCC GCC GTG GTG TCC GCC GTG ATC GCC GCG GCC GCC GCG CAG AGC GGC<br>Ala Ala Val Val Ser Ala Val Ile Ala Ala Ala Ala Ala Gln Ser Gly<br>165 170 175 | | 528 |
| GCG GGC CCG CAC TAC CAC CAC CAC CAC CAC GCC GCC GGC CAC CAC<br>Ala Gly Pro His Tyr His His His His His Ala Ala Gly His His<br>180 185 190 | | 576 |
| CAC CAC CCG ACG GCC GGC GCG CCC GGC GCC GCG GGC AGC GCG GCC GCT<br>His His Pro Thr Ala Gly Ala Pro Gly Ala Ala Gly Ser Ala Ala Ala<br>195 200 205 | | 624 |
| TCG GCC GGT GGC GCT GGG GGC GCG GGC GGC GGT GGC CCG GCC AGC GTT<br>Ser Ala Gly Gly Ala Gly Gly Ala Gly Gly Gly Gly Pro Ala Ser Val<br>210 215 220 | | 672 |
| GGG GGC GGC GGC GGC GGC GGC GGC GGC GGA GGC GGC GGG GGC GCG GCG<br>Gly Gly Gly Gly Gly Gly Gly Gly Gly Gly Gly Gly Gly Gly Ala Ala<br>225 230 235 240 | | 720 |
| GGC GCC CTG CAC CCG CAC CAC GCC GCC GGC GGC CTG CAC TTC GAC GAC<br>Gly Ala Leu His Pro His His Ala Ala Gly Gly Leu His Phe Asp Asp<br>245 250 255 | | 768 |
| CGC TTC TCC GAC GAG CAG CTG GTG ACC ATG TCT GTG CGC GAC TGG AAC<br>Arg Phe Ser Asp Glu Gln Leu Val Thr Met Ser Val Arg Asp Trp Asn<br>260 265 270 | | 816 |
| CGG CAG CTG CGC GGG GTC AGC AAG GAG GAG GTG ATC CGG CTG AAG CAG<br>Arg Gln Leu Arg Gly Val Ser Lys Glu Glu Val Ile Arg Leu Lys Gln<br>275 280 285 | | 864 |
| AAG AGG CGG ACC CTG AAA AAC CGC GGC TAT GCC AAG TCC TGC CGC TTC<br>Lys Arg Arg Thr Leu Lys Asn Arg Gly Tyr Ala Lys Ser Cys Arg Phe<br>290 295 300 | | 912 |
| AAG AGG GTG CAG CAG AGA CAC GTC CTG GAG TCG GAG AAG AAC CAG CTG<br>Lys Arg Val Gln Gln Arg His Val Leu Glu Ser Glu Lys Asn Gln Leu<br>305 310 315 320 | | 960 |
| CTG CAG CAA GTC GAC CAC CTC AAG CAG GAG ATC TCC AGG CTG GTG CGC<br>Leu Gln Gln Val Asp His Leu Lys Gln Glu Ile Ser Arg Leu Val Arg<br>325 330 335 | | 1008 |
| GAG AGG GAC GCG TAC AAG GAG AAA TAC GAG AAG TTG GTG AGC AGC GGC<br>Glu Arg Asp Ala Tyr Lys Glu Lys Tyr Glu Lys Leu Val Ser Ser Gly<br>340 345 350 | | 1056 |
| TTC CGA GAA AAC GGC TCG AGC AGC GAC AAC CCG TCC TCT CCC GAG TTT<br>Phe Arg Glu Asn Gly Ser Ser Ser Asp Asn Pro Ser Ser Pro Glu Phe<br>355 360 365 | | 1104 |
| TTC ATA ACT GAG CCC ACT CGC AAG TTG GAG CCA TCA GTG GGA TAC GCC<br>Phe Ile Thr Glu Pro Thr Arg Lys Leu Glu Pro Ser Val Gly Tyr Ala<br>370 375 380 | | 1152 |
| ACA TTT TGG AAG CCC CAG CAT CGT GTA CTT ACC AGT GTG TTC ACA AAA<br>Thr Phe Trp Lys Pro Gln His Arg Val Leu Thr Ser Val Phe Thr Lys<br>385 390 395 400 | | 1200 |
| TGA | | 1203 |

(2) INFORMATION FOR SEQ ID NO: 2:

(i) SEQUENCE CHARACTERISTICS:
        (A) LENGTH: 400 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Ser Glu Leu Ala Met Ser Asn Ser Asp Leu Pro Thr Ser Pro
1              5              10             15

Leu Ala Met Glu Tyr Val Asn Asp Phe Asp Leu Met Lys Phe Glu Val
            20              25             30

-continued

```
Lys Lys Glu Pro Val Glu Thr Asp Arg Ile Ile Ser Gln Cys Gly Arg
         35                  40                  45

Leu Ile Ala Gly Gly Ser Leu Ser Ser Thr Pro Met Ser Thr Pro Cys
         50                  55                  60

Ser Ser Val Pro Pro Ser Pro Ser Phe Ser Ala Pro Ser Pro Gly Ser
 65                  70                  75                  80

Arg Gly Glu Gln Lys Ala His Leu Glu Asp Tyr Tyr Trp Met Thr Gly
                 85                  90                  95

Tyr Pro Gln Gln Leu Asn Pro Glu Ala Leu Gly Phe Ser Pro Glu Asp
                100                 105                 110

Ala Val Glu Ala Leu Ile Ser Asn Ser His Gln Leu Arg Gly Gly Phe
            115                 120                 125

Asp Gly Tyr Ala Arg Gly Ala Gln Gln Leu Ala Ala Ala Gly Ala
            130                 135                 140

Gly Ala Gly Ala Ser Leu Gly Gly Ser Gly Glu Glu Met Gly Pro Ala
145                 150                 155                 160

Ala Ala Val Val Ser Ala Val Ile Ala Ala Ala Ala Gln Ser Gly
                165                 170                 175

Ala Gly Pro His Tyr His His His His His His Ala Ala Gly His His
                180                 185                 190

His His Pro Thr Ala Gly Ala Pro Gly Ala Ala Gly Ser Ala Ala Ala
            195                 200                 205

Ser Ala Gly Gly Ala Gly Gly Ala Gly Gly Gly Pro Ala Ser Val
    210                 215                 220

Gly Gly Gly Gly Gly Gly Gly Gly Gly Gly Gly Gly Gly Ala Ala
225                 230                 235                 240

Gly Ala Leu His Pro His His Ala Ala Gly Gly Leu His Phe Asp Asp
                245                 250                 255

Arg Phe Ser Asp Glu Gln Leu Val Thr Met Ser Val Arg Asp Trp Asn
            260                 265                 270

Arg Gln Leu Arg Gly Val Ser Lys Glu Glu Val Ile Arg Leu Lys Gln
        275                 280                 285

Lys Arg Arg Thr Leu Lys Asn Arg Gly Tyr Ala Lys Ser Cys Arg Phe
    290                 295                 300

Lys Arg Val Gln Gln Arg His Val Leu Glu Ser Glu Lys Asn Gln Leu
305                 310                 315                 320

Leu Gln Gln Val Asp His Leu Lys Gln Glu Ile Ser Arg Leu Val Arg
                325                 330                 335

Glu Arg Asp Ala Tyr Lys Glu Lys Tyr Glu Lys Leu Val Ser Ser Gly
            340                 345                 350

Phe Arg Glu Asn Gly Ser Ser Ser Asp Asn Pro Ser Ser Pro Glu Phe
        355                 360                 365

Phe Ile Thr Glu Pro Thr Arg Lys Leu Glu Pro Ser Val Gly Tyr Ala
    370                 375                 380

Thr Phe Trp Lys Pro Gln His Arg Val Leu Thr Ser Val Phe Thr Lys
385                 390                 395                 400
```

HUMAN C-MAF COMPOSITIONS AND METHODS OF USE THEREOF

RELATED APPLICATIONS

This application is a divisional of Ser. No. 09/086,010, filed May 27, 1998, now U.S. Pat. No. 6,274,338, which a continuation in part of Ser. No. 09/030,579, filed Feb. 24, 1998, now abandoned.

GOVERNMENT FUNDING

Work described herein was supported, at least in part, under grant AI/AG 37833 awarded by the National Institutes of Health. The U.S. government therefore may have certain rights in this invention.

BACKGROUND OF THE INVENTION

The Maf family of proteins are a sub-family of AP-1/CREB/ATF proteins. The first member of the family to be identified, the v-maf oncogene, was originally isolated from a spontaneous musculoaponeurotic fibrosarcoma of chicken and identified as the transforming gene of the avian retrovirus, AS42 (Nishizawa, M. et al. (1989) *Proc. Natl. Acad. Sci. USA* 86:7711–7715). V-maf encodes a 42 kd basic region/leucine zipper (b-zip) protein with homology to the c-fos and c-jun oncogenes. Its cellular homologue, the c-maf proto-oncogene, which has been isolated from murine cells, has only two structural changes in the coding region from v-maf (Kataoka, K. et al. (1993) *J. Virol.* 67:2133–2141). The maf family includes c-Maf, mafB, a human retina-specific protein Nrl (Swaroop, A. et al. (1992) *Proc. Natl. Acad. Sci. USA* 89:266–270), mafK, mafF, mafG and p18. The latter four, mafK, mafF, mafG and p18, each encode proteins that lack the amino terminal two thirds of c-Maf that contains the transactivating domain ("small maf proteins") (Fujiwara, K. T. et al. (1993) *Oncogene* 8:2371–2380; Igarashi, K. et al. (1995) *J. Biol. Chem.* 270:7615–7624; Andrews, N. C. et al. (1993) *Proc. Natl. Acad. Sci. USA* 90:11488–11492; Kataoka, K. et al. (1995) *Mol. Cell. Biol.* 15:2180–2190).

C-Maf and other Maf family members form homodimers and heterodimers with each other and with Fos and Jun, consistent with the known ability of the AP-1 proteins to pair with each other (Kerppola, T. K. and Curran, T. (1994) *Oncogene* 9:675–684; Kataoka, K. et al. (1994) *Mol. Cell. Biol.* 14:700–712). The DNA target sequence to which c-Maf homodimers bind, termed the c-Maf response element (MARE), is a 13 or 14 bp element which contains a core TRE (T-MARE) or CRE (C-MARE) palindrome respectively. c-Maf has been shown to stimulate transcription from the Purkinje neuron-specific promoter L7 (Kurscher, C. and Morgan, J. I. (1994) *Mol. Cell. Biol.* 15:246–254) and Nrl has been shown to drive expression of the QR1 retina-specific gene (Swaroop, A. et al. (1992) *Proc. Natl. Acad. Sci. USA* 89:266–270). Additionally, the small mafs have been shown to function as repressors of α and β-globin transcription when bound as homodimers but are essential as heterodimeric partners with the erythroid-specific factor p45NF-E2 to activate globin gene transcription (Kataoka, K. et al (1995) *Mol. Cell. Biol.* 15:2180–2190; Igarashi, K. et al. (1994) *Nature* 367:568–572). MafK overexpression has been shown to induce erythroleukemia cell differentiation (Igarashi, K. et al. (1995) *Proc. Natl. Acad. Sci. USA* 92:7445–7449). Moreover, c-Maf has been shown to control the tissue-specific expression of the cytokine interleukin-4 in T helper 2 (Th2) cells (Ho, I-C. et al. (1996) *Cell* 85:973–983).

The nucleotide sequence of the mouse c-maf proto-oncogene, and predicted amino acid sequence for the mouse c-Maf protein, have been described (Kurscher, C. and Morgan, J. I. (1995) *Mol. Cell. Biol.* 15:246–254; and Genbank Accession number S74567). The nucleotide sequence of the chicken c-maf proto-oncogene, and predicted amino acid sequence for the chicken c-Maf protein, also have been described (Kataoka et al., Genbank Accession number D28596). However, these non-human c-Maf compositions may not function optimally in human cells and, moreover, use of these compositions in humans is likely to stimulate an immune response, since the chicken or mouse c-Maf would be recognized as "foreign" by the human immune system. Accordingly, there is still a need for human c-Maf compositions that are suitable for use in humans.

SUMMARY OF THE INVENTION

This invention provides human c-Maf compositions. In particular, this invention provides isolated nucleic acid molecules encoding human c-Maf and isolated human c-Maf protein. Since the c-Maf compositions of the invention are human-derived, they function optimally in human cells (compared with non-human c-Maf compositions) and do not stimulate an immune response in humans.

One aspect of the invention pertains to an isolated nucleic acid molecule comprising a nucleotide sequence encoding human c-Maf. In a preferred embodiment, the nucleic acid molecule comprises the nucleotide sequence of the coding region of the NheI/XbaI insert of plasmid pHu-c-Maf (ATCC Accession No. 98671). In another preferred embodiment, the nucleic acid molecule comprises the nucleotide sequence of SEQ ID NO: 1. In other embodiments, the nucleic acid molecule has at least 98% nucleotide identity, more preferably 99% nucleotide identity, and even more preferably 99.5% nucleotide identity with the nucleotide sequence of SEQ ID NO: 1 or the nucleotide sequence of the NheI/XbaI insert of plasmid pHu-c-Maf (ATCC Accession No. 98671). In yet another embodiment, the nucleic acid molecule comprises the nucleotide sequence of the NheI/XbaI insert of plasmid pHu-c-Maf (ATCC Accession No. 98671).

The isolated nucleic acid molecules of the invention encoding human c-Maf can be incorporated into a vector, such as an expression vector, and this vector can be introduced into a host cell. The invention also provides a method for producing a human c-Maf protein by culturing a host cell of the invention (carrying a hu-c-Maf expression vector) in a suitable medium until a human c-Maf protein is produced. The method can further involve isolating the human c-Maf protein from the medium or the host cell.

Another aspect of the invention pertains to an isolated human c-Maf protein. Preferably, the human c-Maf protein comprises the amino acid sequence encoded by the coding region of the NheI/XbaI insert of plasmid pHu-c-Maf (ATCC Accession No. 98671). In another preferred embodiment, the protein comprises the amino acid sequence of SEQ ID NO: 2. In other embodiments, the protein has at least 98% amino acid identity, more preferably 99% amino identity, and even more preferably 99.5% amino acid identity with SEQ ID NO: 2 or the protein encoded by the coding region of the NheI/XbaI insert of plasmid pHu-c-Maf (ATCC Accession No. 98671).

Fusion proteins, comprising a human c-Maf protein operatively linked to a polypeptide other than human c-Maf, are also encompassed by the invention, as well as antibodies that specifically bind a human c-Maf protein. The antibodies can be, for example, polyclonal antibodies or monoclonal antibodies. In one embodiment, the antibodies are coupled to a detectable substance.

Another aspect of the invention pertains to a nonhuman transgenic animal that contains cells carrying a transgene encoding a human c-Maf protein.

Yet another aspect of the invention pertains to a method for detecting the presence of human c-Maf in a biological sample. The method involves contacting the biological sample with an agent capable of detecting an indicator of human c-Maf activity such that the presence of human c-Maf is detected in the biological sample. The invention also provides a method for modulating human c-Maf activity in a cell comprising, involving contacting the cell with an agent that modulates human c-Maf activity such that human c-Maf activity in the cell is modulated.

Still another aspect of the invention pertains to methods for identifying a compound that modulates the activity of a human c-Maf protein. These methods generally involve:

providing an indicator composition that comprises a human c-Maf protein;

contacting the indicator composition with a test compound; and determining the effect of the test compound on the activity of the human c-Maf protein in the indicator composition to thereby identify a compound that modulates the activity of a human c-Maf protein. In a preferred embodiment, the indicator composition comprises a human c-Maf protein and a DNA molecule to which the human c-Maf protein binds and the effect of the test compound on the activity of the human c-Maf protein is determined by evaluating the binding of the human c-Maf protein to the DNA molecule in the presence and absence of the test compound. In another preferred embodiment, the indicator composition is a cell comprising a human c-Maf protein and a reporter gene responsive to the human c-Maf protein and the effect of the test compound on the activity of the human c-Maf protein is determined by evaluating the expression of the reporter gene in the presence and absence of the test compound. In yet another embodiment, the method further involves the step of determining the effect of the test compound on an immune response to thereby identify a compound that modulates an immune response.

BRIEF DESCRIPTION OF THE DRAWINGS

FIG. 1A–1B is an alignment of the nucleotide sequence of the human c-maf (SEQ ID NO:1) coding region with the mouse c-maf (SEQ ID NO:3) coding region. Nucleotide differences between the two sequences are boxed.

FIG. 2 is an alignment of the amino acid sequence of the human c-Maf protein (SEQ ID NO:2) with the mouse c-Maf protein (SEQ ID NO:4). Amino acid differences between the two sequences are boxed.

DETAILED DESCRIPTION OF THE INVENTION

This invention pertains to human c-Maf compositions, such as isolated nucleic acid molecules encoding human c-Maf and isolated human c-Maf proteins, as well as methods of use therefore. The human compositions of the invention have the advantages that they function optimally in human cells (compared with non-human c-Maf compositions) and do not stimulate an immune response in humans.

So that the invention may be more readily understood, certain terms are first defined.

As used herein, the term "human c-Maf" is intended to encompass proteins that share the distinguishing structural and functional features (described further herein) of the human c-Maf protein encoded by the Nh2I/XbaI insert of plasmid pHu-c-Maf, which was deposited under the provisions of the Budapest Treaty with the American Type Tissue Culture Collection (ATCC), P.O. Box 1549, Manassas, Va. 20108, on Feb. 24, 1998 and assigned ATCC Acession No. 98671, and having the amino acid sequence of SEQ ID NO: 2, including the amino acid residues unique to human c-Maf (as compared to mouse c-Maf), which are boxed in FIG. 2.

As used herein, the term "nucleic acid molecule" is intended to include DNA molecules (e.g., cDNA or genomic DNA) and RNA molecules (e.g., mRNA). The nucleic acid molecule may be single-stranded or double-stranded, but preferably is double-stranded DNA.

An used herein, an "isolated nucleic acid molecule" refers to a nucleic acid molecule that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). For example, in various embodiments, an isolated human c-Maf nucleic acid molecule typically contains less than about 10 kb of nucleotide sequences which naturally flank the nucleic acid molecule in genomic DNA of the cell from which the nucleic acid is derived, and more preferably contains less than about 5, kb, 4 kb, 3 kb, 2 kb, 1 kb, 0.5 kb or 0.1 kb of naturally flanking nucleotide sequences. An "isolated" human c-Maf nucleic acid molecule may, however, be linked to other nucleotide sequences that do not normally flank the human c-Maf sequences in genomic DNA (e.g., the human c-Maf nucleotide sequences may be linked to vector sequences). In certain preferred embodiments, an "isolated" nucleic acid molecule, such as a cDNA molecule, also may be free of other cellular material. However, it is not necessary for the human c-Maf nucleic acid molecule to be free of other cellular material to be considered "isolated" (e.g., a human c-Maf DNA molecule separated from other mammalian DNA and inserted into a bacterial cell would still be considered to be "isolated").

As used herein, the term "hybridizes under high stringency conditions" is intended to describe conditions for hybridization and washing under which nucleotide sequences having substantial homology (e.g., typically greater than 70% homology) to each other remain stably hybridized to each other. A preferred, non-limiting example of high stringency conditions are hybridization in a hybridization buffer that contains 6× sodium chloride/sodium citrate (SSC) at a temperature of about 45° C. for several hours to overnight, followed by one or more washes in a washing buffer containing 0.2×SSC, 0.1% SDS at a temperature of about 50–65° C.

The term "% identity" as used in the context of nucleotide and amino acid sequences (e.g., when one amino acid sequence is said to be X % identical to another amino acid sequence) refers to the percentage of identical residues shared between the two sequences, when optimally aligned. To determine the percent identity of two nucleotide or amino acid sequences, the sequences are aligned for optimal comparison purposes (e.g., gaps may be introduced in one sequence for optimal alignment with the other sequence).

The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/total # of positions× 100).

Computer algorithms known in the art can be used to optimally align and compare two nucleotide or amino acid sequences to define the percent identity between the two sequences. A preferred, non-limiting example of a mathematical algorithim utilized for the comparison of two sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs of Altschul, et al. (1990) J. Mol. Biol. 215:403–10. To obtain gapped alignments for comparison purposes, Gapped BLAST can be utilized as described in Altschul et al., (1997) Nucleic Acids Research 25(17):3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithim utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. If multiple programs are used to compare sequences, the program that provides optimal alignment (i.e., the highest percent identity between the two sequences) is used for comparison purposes.

As used herein, a "naturally-occurring" nucleic acid molecule refers to an RNA or DNA molecule having a nucleotide sequence that occurs in nature (e.g., encodes a natural protein).

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein" refers to a protein that is substantially free of other proteins, cellular material and culture medium when isolated from cells or produced by recombinant DNA techniques, or chemical precursors or other chemicals when chemically synthesized.

As used herein, the term "antibody" is intended to include immunoglobulin molecules and immunologically active portions of immunoglobulin molecules, i.e., molecules that contain an antigen binding site which specifically binds (immunoreacts with) an antigen, such as Fab and F(ab')$_2$ fragments. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody compositions thus typically display a single binding affinity for a particular antigen with which it immunoreacts.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp,D) | GAC, GAT |
| Cysteine (Cys, C) | TGC, TGT |
| Glutamic acid (Glu,E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe,F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for a human c-Maf protein of the invention (or any portion thereof) can be use to derive the human c-Maf amino acid sequence, using the genetic code to translate the DNA or RNA molecule into an amino acid sequence. Likewise, for any human c-Maf-amino acid sequence, corresponding nucleotide sequences that can encode the human c-Maf protein can be deduced from the genetic code (which, because of its redundancy, will produce multiple nucleic acid sequences for any given amino acid sequence). Thus, description and/or disclosure herein of a human c-Maf nucleotide sequence should be considered to also include description and/or disclosure of the amino acid sequence encoded by the nucleotide sequence. Similarly, description and/or disclosure of a human c-Maf amino acid sequence herein should be considered to also include description and/or disclosure of all possible nucleotide sequences that can encode the amino acid sequence.

Various aspects of the invention are described in further detail in the following subsections:

I. Isolated Nucleic Acid Molecules

One aspect of the invention pertains to isolated nucleic acid molecules that encode human c-Maf. An approximately 4.2 kilobase fragment of DNA encoding human c-Maf has been isolated from a genomic DNA library and subcloned into the plasmid pBluescriptKS/II. E. coli bacteria carrying this plasmid, referred to as pHu-c-Maf, have been deposited under the provisions of the Budapest Treaty with the American Type Culture Collection (ATCC), P.O. Box 1549, Manassas, Va. 20108, on Feb. 24, 1998 and assigned ATCC Accession No. 98671. This plasmid was constructed by insertion of a ~4.2 kb NheI fragment encompassing the human c-Maf coding region into the compatible XbaI site of the plasmid vector, to thereby create a ~4.2 kb NheI/XbaI insert that encodes human c-Maf. It should be noted that upon ligation of the NheI fragment into the XbaI site, these restriction sites are not regenerated and, thus, to excise the fragment from the plasmid, it is necessary to use adjacent restriction sites within the pBluescript polylinker. The nucleotide sequence of the human c-Maf coding region, and corresponding predicted amino acid sequence, are shown in SEQ ID NOs: 1 and 2, respectively. This nucleotide sequence, and predicted amino acid sequence, of human c-Maf were obtained by sequencing of the NheI/XbaI insert of the pHu-c-Maf plasmid using standard sequencing methods. Primers for sequencing are designed based on the nucleotide sequence shown in SEQ ID NO: 1. Isolation and characterization of the human c-Maf-encoding DNA is described further in the Example.

In a preferred embodiment, the nucleic acid molecule of the invention comprises the nucleotide sequence of the coding region of the NheI/XbaI insert of plasmid pHu-c-Maf (ATCC Accession No. 98671). In another preferred embodiment, the nucleic acid moleculecomprises the nucleotide sequence of SEQ ID NO: 1. In other embodiments, the nucleic acid molecule has at least 98% nucleotide identity, more preferably 99% nucleotide identity, and even more preferably 99.5% nucleotide identity with the nucleotide sequence of SEQ ID NO: 1 or the nucleotide sequence of the NheI/XbaI insert of plasmid pHu-c-Maf (ATCC Accession No. 98671). In yet another embodiment, the nucleic acid molecule comprising the nucleotide sequence of the NheI/XbaI insert of plasmid pHu-c-Maf (ATCC Accession No. 98671).

Nucleic acid molecules that differ from SEQ ID NO: 1 (and nucleotide sequence of the NheI/XbaI insert of p-Hu-c-Maf) due to degeneracy of the genetic code, and thus encode the same human c-Maf protein as that encoded by SEQ ID NO: 1 and pHu-c-Maf, are encompassed by the invention. Accordingly, in another embodiment, an isolated nucleic acid molecule of the invention has a nucleotide sequence encoding a protein having an amino acid sequence shown in SEQ ID NO: 2 or having the amino acid sequence encoded by the coding region of the NheI/XbaI insert of p-Hu-c-Maf.

A nucleic acid molecule having the nucleotide sequence of human c-Maf can be obtained from plasmid pHu-c-Maf or can be isolated using standard molecular biology techniques and the sequence information provided herein. For example, a human c-Maf DNA can be isolated from a human genomic DNA library using all or portion of SEQ ID NO: 1 as a hybridization probe and standard hybridization techniques (e.g., as described in Sambrook, J., et al. *Molecular Cloning: A Laboratory Manual*. 2nd, ed., Cold Spring Harbor Laboratory, Cold Spring Harbor, N.Y., 1989). Moreover, a nucleic acid molecule encompassing all or a portion of SEQ ID NO: 1 can be isolated by the polymerase chain reaction using oligonucleotide primers designed based upon the sequence of SEQ ID NO: 1. For example, mRNA can be isolated from cells (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a human c-Maf nucleotide sequence can be prepared by standard synthetic techniques, e.g., using an automated DNA synthesizer.

In addition to the human c-Maf nucleotide sequence shown in SEQ ID NO: 1 and carried by plasmid pHu-c-Maf, it will be appreciated by those skilled in the art that DNA sequence polymorphisms that lead to minor changes in the nucleotide or amino acid sequences of human c-Maf may exist within a population. Such genetic polymorphism in the human c-Maf gene may exist among individuals within a population due to natural allelic variation. Such natural allelic variations can typically result in 1–2% variance in the nucleotide sequence of the a gene. Any and all such nucleotide variations and resulting amino acid polymorphisms in human c-Maf that are the result of natural allelic variation and that do not alter the functional activity of human c-Maf are intended to be within the scope of the invention.

Nucleic acid molecules corresponding to natural allelic variants of the human c-Maf DNAs of the invention can be isolated based on their homology to the human c-Maf nucleic acid molecules disclosed herein using the human DNA, or a portion thereof, as a hybridization probe according to standard hybridization techniques under high stringency hybridization conditions. Accordingly, in another embodiment, an isolated nucleic acid molecule of the invention hybridizes under high stringency conditions to a second nucleic acid molecule comprising the nucleotide sequence of SEQ ID NO: 1. In certain embodiment, the isolated nucleic acid molecule comprises at least 30, 50, 100, 200, 300, 400, 500, 600, 700, 800, 900, 1000, 2000 or 3000 contiguous nucleotides of SEQ ID NO: 1. Preferably, an isolated nucleic acid molecule of the invention that hybridizes under high stringency conditions to the sequence of SEQ ID NO: 1 corresponds to a naturally-occurring allelic variant of a human c-Maf nucleic acid molecule.

In addition to naturally-occurring allelic variants of the human c-Maf sequence that may exist in the population, the skilled artisan will further appreciate that minor changes may be introduced by mutation into the nucleotide sequence of SEQ ID NO: 1, thereby leading to changes in the amino acid sequence of the encoded protein, without altering the functional activity of the human c-Maf protein. For example, nucleotide substitutions leading to amino acid substitutions at "non-essential" amino acid residues may be made in the sequence of SEQ ID NO: 1. A "non-essential" amino acid residue is a residue that can be altered from the wild-type sequence of human c-Maf (e.g., the sequence of SEQ ID NO: 2) without altering the functional activity of c-Maf, such as its ability to interact with DNA or its ability to enhance transcription from an IL-4 promoters whereas an "essential" amino acid residue is required for functional activity.

Accordingly, another aspect of the invention pertains to nucleic acid molecules encoding human c-Maf proteins that contain changes in amino acid residues that are not essential for human c-Maf activity. Such human c-Maf proteins differ in amino acid sequence from SEQ ID NO: 2 (or the amino acid sequence encoded by pHu-c-Maf) yet retain human c-Maf activity. These non-natural variants of human c-Maf also differ from non-human c-Maf proteins (e.g., chicken or mouse c-Maf) in that they encode at least one amino acid residue that is unique to human c-Maf (i.e., at least one residue that is not present in chicken or mouse c-Maf). Preferably, these non-natural variants of human c-Maf encode at least 2, 3, 4, 5, 6, 7, 8, 9 or 10 amino acid residues that are unique to human c-Maf (i.e., that are not present in chicken or mouse c-Maf).

An isolated nucleic acid molecule encoding a non-natural variant of a human c-Maf protein can be created by introducing one or more nucleotide substitutions, additions or deletions into the nucleotide sequence of SEQ ID NO: 1 (or plasmid pHu-c-Maf) such that one or more amino acid substitutions, additions or deletions are introduced into the encoded protein. Mutations can be introduced into SEQ ID NO: 1 by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in human c-Maf is preferably replaced with another amino acid residue from the same side chain family. Alternatively, in another embodiment, mutations can be introduced randomly along all or part of the human c-Maf coding sequence, such as by saturation mutagenesis, and the resultant mutants can be screened for their ability to bind to DNA and/or activate transcription, to identify mutants that retain functional activity. Following mutagenesis, the encoded human c-Maf mutant protein can be expressed recombinantly in a host cell and the functional activity of the mutant protein can be determined using assays available in the art for assessing c-Maf activity (e.g., assays such as those described in detail in PCT Publication WO 97/39721.

Another aspect of the invention pertains to isolated nucleic acid molecules that are antisense to the coding strand of a human c-Maf mRNA or gene. An antisense nucleic acid of the invention can be complementary to an entire human c-Maf coding strand, or to only a portion thereof. In one embodiment, an antisense nucleic acid molecule is antisense to a coding region of the coding strand of a nucleotide sequence encoding human c-Maf that is unique to human c-Maf (as compared to non-human c-Mafs, such as chicken or mouse c-Maf). In another embodiment, the antisense nucleic acid molecule is antisense to a noncoding region of the coding strand of a nucleotide sequence encoding human c-Maf that is unique to human c-Maf (as compared to non-human c-Mafs, such as chicken or mouse c-Maf). In preferred embodiments, an antisense of the invention comprises at least 30 contiguous nucleotides of the noncoding strand of SEQ ID NO: 1, more preferably at least 50, 100, 200, 300, 400, 500, 600, 700, 800, 900 or 1000 contiguous nucleotides of the noncoding strand of SEQ ID NO: 1.

Given the coding strand sequences encoding human c-Maf disclosed herein (e.g., SEQ ID NO: 1 and plasmid pHu-c-Maf), antisense nucleic acids of the invention can be designed according to the rules of Watson and Crick base pairing. The antisense nucleic acid molecule may be complementary to the entire coding region of human c-Maf mRNA, or alternatively can be an oligonucleotide which is antisense to only a portion of the coding or noncoding region of human c-Maf mRNA. For example, the antisense oligonucleotide may be complementary to the region surrounding the translation start site of human c-Maf mRNA. An antisense oligonucleotide can be, for example, about 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for a human c-Maf-encoding nucleic acid can be designed based upon the nucleotide sequence of a human c-Maf gene disclosed herein. For example, a derivative of a *Tetrahymena* L-19 IVS RNA can be constructed in which the base sequence of the active site is complementary to the base sequence to be cleaved in a human c-Maf-encoding mRNA. See for example Cech et al. U.S. Pat. No. 4,987,071; and Cech et al. U.S. Pat. No. 5,116,742. Alternatively, human c-Maf mRNA can be used to select a catalytic RNA having a specific ribonuclease activity from a pool of RNA molecules. See for example Bartel, D. and Szostak, J. W. (1993) *Science* 261: 1411–1418.

Yet another aspect of the invention pertains to isolated nucleic acid molecules encoding human c-Maf fusion proteins. Such nucleic acid molecules, comprising at least a first nucleotide sequence encoding a human c-Maf protein, polypeptide or peptide operatively linked to a second nucleotide sequence encoding a non-human c-Maf protein, polypeptide or peptide, can be prepared by standard recombinant DNA techniques. Human c-Maf fusion proteins are described in further detail below in subsection III.

II. Recombinant Expression Vectors and Host Cells

Another aspect of the invention pertains to vectors, preferably recombinant expression vectors, containing a nucleic acid encoding human c-Maf (or a portion thereof). The expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., human c-Maf proteins, mutant forms of human c-Maf proteins, human c-Maf fusion proteins and the like).

The recombinant expression vectors of the invention can be designed for expression of human c-Maf protein in prokaryotic or eukaryotic cells. For example, human c-Maf can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promotors directing the expression of either fusion or non-fusion proteins. Fusion vectors add a number of amino acids to a protein encoded therein, usually to the amino terminus of the recombinant protein. Such fusion vectors can serve one or more purposes: 1) to increase expression of recombinant protein; 2) to increase the solubility of the recombinant protein; 3) to aid in the purification of the recombinant protein by acting as a ligand in affinity purification; 4) to provide an epitope tag to aid in detection and/or purification of the protein; and/or 5) to provide a marker to aid in detection of the protein (e.g., a color marker using β-galactosidase fusions). Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc.; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Recombinant proteins also can be expressed in eukaryotic cells as fusion proteins for the same purposes discussed above.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res.* 20:2111–2118). Such alteration of nucleic acid sequences of the invention can be carried out by standard DNA synthesis techniques.

In another embodiment, the human c-Maf expression vector is a yeast expression vector. Examples of vectors for expression in yeast *S. cerivisae* include pYepSec1 (Baldari. et al., (1987) *EMBO J.* 6:229–234), pMFa (Kurjan and Herskowitz, (1982) *Cell* 30:933–943), pJRY88 (Schultz et al, (1987) *Gene* 54:113–123), and pYES2 (Invitrogen Corporation, San Diego, Calif.).

Alternatively, human c-Maf can be expressed in insect cells using baculovirus expression vectors. Baculovirus vectors available for expression of proteins in cultured insect cells (e.g., Sf9 cells) include the pAc series (Smith et al., (1983) *Mol. Cell Biol.* 3:2156–2165) and the pVL series (Lucklow, V. A., and Summers, M. D., (1989) *Virology* 170:31–39).

In yet another embodiment, a nucleic acid of the invention is expressed in mammalian cells using a mammalian expression vector. Examples of mammalian expression vectors include pMex-NeoI, pCDM8 (Seed, B., (1987) *Nature* 329:840) and pMT2PC (Kaufman et al. (1987), *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), the albumin promoter (liver-specific; Pinkert et al. (1987) *Genes Dev.* 1:268–277), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Moreover, inducible regulatory systems for use in mammalian cells are known in the art, for example systems in which gene expression is regulated by heavy metal ions (see e.g., Mayo et al. (1982) *Cell* 29:99–108; Brinster et al. (1982) *Nature* 296:39–42; Searle et al. (1985) *Mol. Cell. Biol.* 5:1480–1489), heat shock (see e.g., Nouer et al. (1991) in *Heat Shock Response*, e.d. Nouer, L., CRC, Boca Raton, Fla., pp167–220), hormones (see e.g., Lee et al. (1981) *Nature* 294:228–232; Hynes et al. (1981) *Proc. Natl. Acad. Sci. USA* 78:2038–2042; Klock et al. (1987) *Nature* 329:734–736; Israel & Kaufman (1989) *Nucl. Acids Res.* 17:2589–2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547–5551; Gossen, M. et al. (1995) *Science* 268:1766–1769; PCT Publication No. WO 94/29442; and PCT Publication No. WO 96/01313). Accordingly, in another embodiment, the invention provides a recombinant expression vector in which human c-Maf DNA is operatively linked to an inducible eukaryotic promoter, thereby allowing for inducible expression of human c-Maf protein in eukaryotic cells.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to human c-Maf mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to recombinant host cells into which a vector, preferably a recombinant expression vector, of the invention has been introduced. A host cell may be any prokaryotic or eukaryotic cell. For example, human c-Maf protein may be expressed in bacterial cells such as *E. coli*, insect cells, yeast or mammalian cells (such as Chinese hamster ovary cells (CHO) or COS cells). Other suitable host cells are known to those skilled in the art. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same vector as that encoding human c-Maf or may be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) human c-Maf protein. Accordingly, the invention further provides methods for producing human c-Maf protein using the host cells of the invention. In one embodiment, the method comprises culturing the host cell of invention (into which a recombinant expression vector encoding human c-Maf has been introduced) in a suitable medium until human c-Maf is produced. In another embodiment, the method further comprises isolating human c-Maf from the medium or the host cell. In its native form the human c-Maf protein is an intracellular protein and, accordingly, recombinant human c-Maf protein can be expressed intracellularly in a recombinant host cell and then isolated from the host cell, e.g., by lysing the host cell and recovering the recombinant human c-Maf protein from the lysate. Alternatively, recombinant human c-Maf protein can be prepared as a extracellular protein by operatively linking a heterologous signal sequence to the amino-terminus of the protein such that the protein is secreted from the host cells. In this case, recombinant human c-Maf protein can be recovered from the culture medium in which the cells are cultured.

Certain host cells of the invention can also be used to produce nonhuman transgenic animals. For example, in one embodiment, a host cell of the invention is a fertilized oocyte or an embryonic stem cell into which human c-Maf-coding sequences have been introduced. Such host cells can then be used to create non-human transgenic animals in which exogenous human c-Maf sequences have been introduced into their genome or homologous recombinant animals in which endogenous c-Maf sequences have been altered. Such animals are useful for studying the function and/or activity of human c-Maf and for identifying and/or evaluating modulators of human c-Maf activity. Accordingly, another aspect of the invention pertains to nonhuman transgenic animals which contain cells carrying a transgene encoding a human c-Maf protein or a portion of a human c-Maf protein. In a subembodiment, of the transgenic animals of the invention, the transgene alters an endogenous gene encoding an endogenous c-Maf protein (e.g., homologous recombinant animals in which the endogenous c-Maf gene has been functionally disrupted or "knocked out", or the nucleotide sequence of the endogenous c-Maf gene has been mutated or the transcriptional regulatory region of the endogenous c-Maf gene has been altered).

A transgenic animal of the invention can be created by introducing human c-Maf-encoding nucleic acid into the male pronuclei of a fertilized oocyte, e.g., by microinjection, and allowing the oocyte to develop in a pseudopregnant female foster animal. The human c-Maf nucleotide sequence of SEQ ID NO: 1 (and plasmid pHu-c-Maf) can be introduced as a transgene into the genome of a non-human animal. Intronic sequences and polyadenylation signals can also be included in the transgene to increase the efficiency of expression of the transgene. A tissue-specific regulatory sequence(s) can be operably linked to the human c-Maf transgene to direct expression of human c-Maf protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the human c-Maf transgene in its genome and/or expression of human c-Maf mRNA in tissues or cells of the animals. A transgenic founder animal can then be used to breed additional animals carrying the transgene. Moreover, transgenic animals carrying a transgene encoding human c-Maf can further be bred to other transgenic animals carrying other transgenes.

To create a homologous recombinant animal, a vector is prepared which contains at least a portion of a human c-Maf gene into which a deletion, addition or substitution has been introduced to thereby alter, e.g., functionally disrupt, the endogenous c-Maf gene. In one embodiment, a homologous recombination vector is designed such that, upon homologous recombination, the endogenous c-Maf gene is functionally disrupted (i.e., no longer encodes a functional protein; also referred to as a "knock out" vector). Alternatively, the vector can be designed such that, upon homologous recombination, the endogenous c-Maf gene replaced by the human c-Maf gene. In the homologous recombination vector, the altered portion of the c-Maf gene is flanked at its 5' and 3' ends by additional nucleic acid of the c-Maf gene to allow for homologous recombination to occur between the exogenous human c-Maf gene carried by the vector and an endogenous c-Maf gene in an embryonic stem cell. The additional flanking c-Maf nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced human c-Maf gene has homologously recombined with the endogenous c-Maf gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In addition to the foregoing, the skilled artisan will appreciate that other approaches known in the art for homologous recombination can be applied to the instant invention. Enzyme-assisted site-specific integration systems are known in the art and can be applied to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nucl. Acids Res.* 21:2025–2029; and Fukushige, S. and Sauer, B. (1992) *Proc. Natl. Acad. Sci. USA* 89:7905–7909) and the FLP recombinase-FRT target system (e.g., as described in Dang, D. T. and Perrimon, N. (1992) *Dev. Genet.* 13:367–375; and Fiering, S. et al. (1993) *Proc. Natl. Acad. Sci. USA* 90:8469–8473). Tetracycline-regulated inducible homologous recombination systems, such as described in PCT Publication No. WO 94/29442 and PCT Publication No. WO 96/01313, also can be used.

III. Isolated Human c-Maf Proteins and Anti-Human c-Maf Antibodies

Another aspect of the invention pertains to isolated human c-Maf proteins. Preferably, the human c-Maf protein comprises the amino acid sequence encoded by the coding region of the NheI/XbaI insert of plasmid pHu-c-Maf (ATCC Accession No. 98671). In another preferred embodiment, the protein comprises the amino acid sequence of SEQ ID NO: 2. In other embodiments, the protein has at least 98% amino acid identity, more preferably 99% amino identity, and even more preferably 99.5% amino acid identity with SEQ ID NO: 2 or the protein encoded by the coding region of the NheI/XbaI insert of plasmid pHu-c-Maf (ATCC Accession No. 98671).

In other embodiments, the invention provides isolated portions of the human c-Maf protein. For example, the invention further encompasses an amino-terminal portion of human c-Maf that includes a transcriptional activation domain. In various embodiments, this amino terminal portion encompasses at least amino acids 1–122, at least amino acids 1–187, or at least amino acids 1–257. Another isolated portion of human c-Maf provided by the invention is a portion encompassing a carboxy-terminal leucine zipper domain. This portion encompasses at least amino acids 313–348.

Human c-Maf proteins of the invention are preferably produced by recombinant DNA techniques. For example, a nucleic acid molecule encoding the protein is cloned into an expression vector (as described above), the expression vector is introduced into a host cell (as described above) and the human c-Maf protein is expressed in the host cell. The human c-Maf protein can then be isolated from the cells by an appropriate purification scheme using standard protein purification techniques. Alternative to recombinant expression, a human c-Maf polypeptide can be synthesized chemically using standard peptide synthesis techniques. Moreover, native human c-Maf protein can be isolated from cells (e.g., from T cells), for example by immunoprecipitation using an anti-human c-Maf antibody.

The invention also provides human c-Maf fusion proteins. As used herein, a human c-Maf "fusion protein" comprises a human c-Maf polypeptide operatively linked to a polypeptide other than human c-Maf. A "human c-Maf polypeptide" refers to a polypeptide having an amino acid sequence corresponding to human c-Maf protein, or a peptide fragment thereof which is unique to human c-Maf protein (as compared to non-human c-Maf proteins, such as mouse or chicken c-Maf", whereas a "polypeptide other than human c-Maf" refers to a polypeptide having an amino acid sequence corresponding to another protein. Within the fusion protein, the term "operatively linked" is intended to indicate that the human c-Maf polypeptide and the other polypeptide are fused in-frame to each other. The other polypeptide may be fused to the N-terminus or C-terminus of the human c-Maf polypeptide. For example, in one embodiment, the fusion protein is a GST-human c-Maf fusion protein in which the human c-Maf sequences are fused to the C-terminus of the GST sequences. In another embodiment, the fusion protein is a human c-Maf-HA fusion protein in which the human c-Maf nucleotide sequence is inserted in a vector such as pCEP4-HA vector (Herrscher, R. F. et al. (1995) *Genes Dev.* 9:3067–3082) such that the human c-Maf sequences are fused in frame to an influenza hemagglutinin epitope tag. Such fusion proteins can facilitate the purification of recombinant human c-Maf.

Preferably, a human c-Maf fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A human c-Maf-encoding nucleic acid can be cloned into such an expression vector such that the fusion moiety is linked in-frame to the human c-Maf protein.

An isolated human c-Maf protein, or fragment thereof, can be used as an immunogen to generate antibodies that bind specifically to human c-Maf using standard techniques for polyclonal and monoclonal antibody preparation. The human c-Maf protein can be used to generate antibodies or, alternatively, an antigenic peptide fragment of human c-Maf can be used as the immunogen. An antigenic peptide fragment of human c-Maf typically comprises at least 8 amino acid residues of the amino acid sequence shown in SEQ ID NO: 2 and encompasses an epitope of human c-Maf such that an antibody raised against the peptide forms a specific immune complex with human c-Maf. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of human c-Maf that are located on the surface of the protein, e.g., hydrophilic regions, and that are unique to human c-Maf, as compared to c-Maf proteins from other species, such as chicken or mouse (i.e., an antigenic peptide that spans a region of human c-Maf that is not conserved across species is used as immunogen; such non-conserved regions/residues are boxed in FIG. 2). A standard hydrophobicity analysis of the human c-Maf protein can be performed to identify hydrophilic regions.

A human c-Maf immunogen typically is used to prepare antibodies by immunizing a suitable subject, (e.g., rabbit, goat, mouse or other mammal) with the immunogen. An appropriate immunogenic preparation can contain, for examples, recombinantly expressed human c-Maf protein or a chemically synthesized human c-Maf peptide. The preparation can further include an adjuvant, such as Freund's complete or incomplete adjuvant, or similar immunostimulatory agent. Immunization of a suitable subject with an immunogenic human c-Maf preparation induces a polyclonal anti-human c-Maf antibody response.

Accordingly, another aspect of the invention pertains to anti-human c-Maf antibodies. Polyclonal anti-human c-Maf antibodies can be prepared as described above by immunizing a suitable subject with a human c-Maf immunogen. The anti-human c-Maf antibody titer in the immunized subject can be monitored over time by standard techniques, such as with an enzyme linked immunosorbent assay (ELISA) using immobilized human c-Maf. If desired, the antibody molecules directed against human c-Maf can be isolated from the mammal (e.g., from the blood) and further purified by well known techniques, such as protein A chromatography to obtain the IgG fraction. At an appropriate time after immunization, e.g., when the anti-human c-Maf antibody titers are highest, antibody-producing cells can be obtained from the subject and used to prepare monoclonal antibodies by standard techniques, such as the hybridoma technique originally described by Kohler and Milstein (1975, *Nature* 256:495–497) (see also, Brown et al (1981) *J. Immunol* 127:539–46; Brown et al. (1980) *J Biol Chem* 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.*, 3:231–36). Briefly, an immortal cell line (typically a myeloma) is fused to lymphocytes (typically splenocytes) from a mammal immunized with a human c-Maf immunogen as described above, and the culture supernatants of the resulting hybridoma cells are screened to identify a hybridoma producing a monoclonal antibody that binds specifically to human c-Maf.

Any of the many well known protocols used for fusing lymphocytes and immortalized cell lines can be applied for the purpose of generating an anti-human c-Maf monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind human c-Maf, e.g., using a standard ELISA assay.

Alternative to preparing monoclonal antibody-secreting hybridomas, a monoclonal anti-human c-Maf antibody can be identified and isolated by screening a recombinant combinatorial immunoglobulin library (e.g., an antibody phage display library) with human c-Maf to thereby isolate immunoglobulin library members that bind human c-Maf. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J* 12:725–734; Hawkins et al (1992) *J Mol Biol* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; Barbas et al. (1991) *PNAS* 88:7978–7982; and McCafferty et al *Nature* (1990) 348:552–554.

Additionally, recombinant anti-human c-Maf antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184,187; Taniguchi, M., European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-human c-Maf antibody (e.g., monoclonal antibody) can be used to isolate human c-Maf by standard techniques, such as affinity chromatography or immunoprecipitation. An anti-human c-Maf antibody can facilitate the purification of natural human c-Maf from cells and of recombinantly produced human c-Maf expressed in host cells. Moreover, an anti-human c-Maf antibody can be used to detect human c-Maf protein (e.g., in a cellular lysate or cell supernatant). Detection may be facilitated by coupling (i.e., physically linking) the antibody to a detectable substance. Accordingly, in one embodiment, an anti-human c-Maf antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

Yet another aspect of the invention pertains to anti-human c-Maf antibodies that are obtainable by a process comprising:

(a) immunizing an animal with an immunogenic human c-Maf protein, or an immunogenic portion thereof unique to human c-Maf protein; and (b) isolating from the animal antibodies that specifically bind to a human c-Maf protein.

Methods for immunization and recovery of the specific anti-human c-Maf antibodies are described further above.

IV. Pharmaceutical Compositions

Human c-Maf modulators of the invention (e.g., human c-Maf inhibitory or stimulatory agents, including human c-Maf proteins and antibodies) can be incorporated into pharmaceutical compositions suitable for administration. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

V. Methods of the Invention

Another aspect of the invention pertains to methods of using the various human c-Maf compositions of the invention. For example, the invention provides a method for detecting the presence of human c-Maf activity in a biological sample. The method involves contacting the biological sample with an agent capable of detecting human c-Maf activity, such as human c-Maf protein or human c-Maf mRNA, such that the presence of human c-Maf activity is detected in the biological sample.

A preferred agent for detecting human c-Maf mRNA is a labeled nucleic acid probe capable of specifically hybridizing to human c-Maf mRNA. The nucleic acid probe can be, for example, the human c-Maf DNA of SEQ ID NO: 1 (or plasmid pHu-c-Maf), or a portion thereof unique to human c-Maf (as compared to c-Maf from other species, such as chicken or mouse), such as an oligonucleotide of at least 15, 30, 50, 100, 200, 300, 400, 500, 600, 700, 800, 900 or 1000 nucleotides in length and sufficient to specifically hybridize under stringent conditions to human c-Maf mRNA.

A preferred agent for detecting human c-Maf protein is a labeled antibody capable of binding to human c-Maf protein. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids. For example, techniques for detection of human c-Maf mRNA include Northern hybridizations and in situ hybridizations. Techniques for detection of human c-Maf protein include enzyme linked immunosorbent assays (ELISAs), Western blots, immunoprecipitations and immunofluorescence.

The invention further provides methods for identifying compounds that modulate the activity of a human c-Maf protein. For example, the invention provides a method for identifying a compound that modulates the activity of a human c-Maf protein, comprising providing an indicator composition that comprises a human c-Maf protein;

contacting the indicator composition with a test compound; and determining the effect of the test compound on the activity of the human c-Maf protein in the indicator composition to thereby identify a compound that modulates the activity of a human c-Maf protein.

Specific embodiments of the screening methods of the invention exploit the ability of c-Maf proteins to bind to DNA (e.g., the ability to bind to a Maf Response Element (MARE)) and/or to regulate gene expression (e.g., regulate expression of a Th2-associated cytokine gene). For further description of these activities of Maf proteins, in general, see for example PCT Publication WO 97/39721, Kurschner and Morgan (1995) Mol. Cell. Biol., 15:246–254; Kataoka et al. (1993) J. Virol. 67:2133–2141; Kataoka et al. (1996) Oncogene 12:53–62; Kataoka et al. (1994) Mol. Cell. Biol. 14:700–712; and Ho, I-C. et al. (1996) Cell 85:973–983; the contents of each of which are expressly incorporated herein by reference.

In a preferred embodiment of the screening assays of the invention, the indicator composition comprises an indicator cell, wherein said indicator cell comprises: (i) the a human c-Maf protein and (ii) a reporter gene responsive to the human c-Maf protein. Preferably, the indicator cell contains:

i) a recombinant expression vector encoding the human c-Maf; and ii) a vector comprising regulatory sequences of a Th2-associated cytokine gene operatively linked a reporter gene; and said method comprises:

a) contacting the indicator cell with a test compound;

b) determining the level of expression of the reporter gene in the indicator cell in the presence of the test compound; and c) comparing the level of expression of the reporter gene in the indicator cell in the presence of the test compound with the level of expression of the reporter gene in the indicator cell in the absence of the test compound to thereby identify a compound that modulates the activity of human c-Maf.

In another preferred embodiment, the indicator composition comprises a preparation of: (i) a human c-Maf protein and (ii) a DNA molecule to which the human c-Maf binds, and said method comprises:

a) contacting the indicator composition with a test compound;

b) determining the degree of interaction of the human c-Maf protein and the DNA molecule in the presence of the test compound; and c) comparing the degree of interaction of the human c-Maf and the DNA molecule in the presence of the test compound with the degree of interaction of the human c-Maf protein and the DNA molecule in the absence of the test compound to thereby identify a compound that modulates the activity of human c-Maf.

Preferably, the DNA molecule to which human c-Maf binds comprises a maf response element (MARE).

In another preferred embodiment, the method identifies proteins that interact with human c-Maf. In this embodiment, the indicator composition is an indicator cell, which indicator cell comprises:
  i) a reporter gene operably linked to a transcriptional regulatory sequence; and
  ii) a first chimeric gene which encodes a first fusion protein, said first fusion protein including human c-Maf;

the test compound comprises a library of second chimeric genes, which library encodes second fusion proteins;

expression of the reporter gene being sensitive to interactions between the first fusion protein, the second fusion protein and the transcriptional regulatory sequence; and wherein the effect of the test compound on human c-Maf in the indicator composition is determined by determining the level of expression of the reporter gene in the indicator cell to thereby identify a test compound comprising a protein that interacts with human c-Maf.

In a preferred embodiment, the library of second chimeric genes is prepared from cDNA library from Th2 cells.

In a preferred embodiment of the screening assays of the invention, once a test compound is identified as modulating the activity of human c-Maf, the effect of the test compound on an immune response is then tested. Accordingly, the screening methods of the invention can further comprise determining the effect of the compound on an immune response to thereby identify a compound that modulates an immune response. In one embodiment, the effect of the compound on an immune response is determined by determining the effect of the compound on expression of a Th2-associated cytokine gene, such as an interleukin-4 gene. As used herein, the term "Th2-associated cytokine" is intended to refer to a cytokine that is produced preferentially or exclusively by Th2 cells rather than by Th1 cells. Examples of Th2-associated cytokines include IL-4, IL-5, IL-6 and IL-13. In another embodiment, the effect of the compound of interest on an immune response is determined by determining the effect of the compound on development of T helper type 1 (Th1) or T helper type 2 (Th2) cells.

Recombinant expression vectors that can be used for expression of human c-Maf in the indicator cell are known in the art (see discussions above). In one embodiment, within the expression vector the human c-Maf-coding sequences are operatively linked to regulatory sequences that allow for constitutive expression of human c-Maf in the indicator cell (e.g., viral regulatory sequences, such as a cytomegalovirus promoter/enhancer, can be used). Use of a recombinant expression vector that allows for constitutive expression of human c-Maf in the indicator cell is preferred for identification of compounds that enhance or inhibit the activity of human c-Maf. In an alternative embodiment, within the expression vector the human c-Maf-coding sequences are operatively linked to regulatory sequences of the endogenous human c-Maf gene (i.e., the promoter regulatory region derived from the endogenous human c-Maf gene). Use of a recombinant expression vector in which human c-Maf expression is controlled by the endogenous regulatory sequences is preferred for identification of compounds that enhance or inhibit the transcriptional expression of human c-Maf.

In methods in which a Th2-associated cytokine gene is utilized (e.g., as a reporter gene), preferably, the Th2-associated cytokine is interleukin-4. It has previously shown that Th2-specific, inducible IL-4 expression can be directed by as little as 157 bp of the proximal IL-4 promoter in Th2 cells (Hodge, M. et al. (1995) *J. Immunol.* 154:6397–6405). Accordingly, in one embodiment, a method of the invention utilizes a reporter gene construct containing this region of the proximal IL-4 promoter, most preferably nucleotides −157 to +58 (relative to the start site of transcription at +1) of the IL-4 promoter. Alternatively, stronger reporter gene expression can be achieved using a longer portion of the IL-4 upstream regulatory region, such as about 3 kb of upstream regulatory sequences. Suitable reporter gene constructs are described in Todd, M. et al. (1993) *J. Exp. Med.* 177:1663–1674. See also PCT Publication WO 97/39721.

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art.

A variety of cell types are suitable for use as an indicator cell in the screening assay. Preferably a cell line is used which does not normally express human c-Maf, such as a B cell (e.g., the M12 B lymphoma cell line) or a Th1 cell clone (e.g., AE7 cells). Nonlymphoid cell lines can also be used as indicator cells, such as the HepG2 hepatoma cell line. Yeast cells also can be used as indicator cells.

In one embodiment, the level of expression of the reporter gene in the indicator cell in the presence of the test compound is higher than the level of expression of the reporter gene in the indicator cell in the absence of the test compound and the test compound is identified as a compound that stimulates the expression or activity of human c-Maf. In another embodiment, the level of expression of the reporter gene in the indicator cell in the presence of the test compound is lower than the level of expression of the reporter gene in the indicator cell in the absence of the test compound and the test compound is identified as a compound that inhibits the expression or activity of human c-Maf.

Alternative to the use of a reporter gene construct, compounds that modulate the expression or activity of human c-Maf can be identified by using other "read-outs." For example, an indicator cell can be transfected with a human c-Maf expression vector, incubated in the presence and in the absence of a test compound, and Th2-associated cytokine production can be assessed by detecting cytokine mRNA (e.g., IL-4 mRNA) in the indicator cell or cytokine secretion (i.e., IL-4 secretion) into the culture supernatant. Standard methods for detecting cytokine mRNA, such as reverse transcription-polymerase chain reaction (RT-PCR) are known in the art. Standard methods for detecting cytokine protein in culture supernatants, such as enzyme linked immunosorbent assays (ELISA) are also known in the art.

As described above, the invention provides a screening assay for identifying proteins (e.g., proteins in Th2 cells) that interact with human c-Maf. These assays can be designed based on the two-hybrid assay system (also referred to as an interaction trap assay) known in the art (see e.g., Field U.S. Pat. No. 5,283,173; Zervos et al. (1993) *Cell* 72:223–232; Madura et al. (1993) *J. Biol. Chem.* 268:12046–12054; Bartel et al. (1993) *Biotechniques*

14:920–924; and Iwabuchi et al. (1993) *Oncogene* 8:1693–1696). The two-hybrid assay is generally used for identifying proteins that interact with a particular target protein. The assay employs gene fusions to identify proteins capable of interacting to reconstitute a functional transcriptional activator. The transcriptional activator consists of a DNA-binding domain and a transcriptional activation domain, wherein both domains are required to activate transcription of genes downstream from a target sequence (such as an upstream activator sequence (UAS) for GAL4). DNA sequences encoding a target "bait" protein are fused to either of these domains and a library of DNA sequences is fused to the other domain. "Fish" fusion proteins (generated from the fusion library) capable of binding to the target-fusion protein (e.g., a target GAL4-fusion "bait") will generally bring the two domains (DNA-binding domain and transcriptional activation domain) into close enough proximity to activate the transcription of a reporter gene inserted downstream from the target sequence. Thus, the "fish" proteins can be identified by their ability to reconstitute a functional transcriptional activator (e.g., a functional GAL4 transactivator).

This general two-hybrid system can be applied to the identification of proteins in cells (e.g., Th2 cells) that interact with human c-Maf by construction of a target human c-Maf fusion protein (e.g., a human c-Maf/GAL4 binding domain fusion as the "bait") and a cDNA library of "fish" fusion proteins (e.g., a cDNA/GAL4 activation domain library), wherein the cDNA library is prepared from mRNA of a cell type of interest (e.g., Th2 cells), and introducing these constructs into a host cell that also contains a reporter gene construct linked to a regulatory sequence responsive to human c-Maf (e.g., a MARE sequence, for example a region of the IL-4 promoter, as discussed above). cDNAs encoding proteins that interact with human c-Maf can be identified based upon transactivation of the reporter gene construct.

Alternatively, a "single-hybrid" assay, such as that described in Sieweke, M. H. et al. (1996) *Cell* 85:49–60, can be used to identify proteins that interact with human c-Maf. This assay is a modification of the two-hybrid system discussed above. In this system, the "bait" is a transcription factor from which the transactivation domain has been removed (e.g., human c-Maf from which the amino-terminal transactivation domain has been removed) and the "fish" is a non-fusion cDNA library (e.g., a cDNA library prepared from Th2 cells). These constructs are introduced into host cells (e.g., yeast cells) that also contains a reporter gene construct linked to a regulatory sequence responsive to human c-Maf (e.g., a MARE sequence, for example a region of the IL-4 promoter, responsive to human c-Maf). cDNAs encoding proteins that interact with human c-Maf can be identified based upon transactivation of the reporter gene construct.

As described above, the invention provides a screening assay for identifying compounds that modulate the interaction of human c-Maf and a MARE (e.g., a MARE in an IL-4 gene regulatory region). Assays are known in the art that detect the interaction of a DNA binding protein with a target DNA sequence (e.g., electrophoretic mobility shift assays, DNAse I footprinting assays and the like). By performing such assays in the presence and absence of test compounds, these assays can be used to identify compounds that modulate (e.g., inhibit or enhance) the interaction of the DNA binding protein with its target DNA sequence.

In one embodiment, the amount of binding of human c-Maf to the DNA fragment in the presence of the test compound is greater than the amount of binding of human c-Maf to the DNA fragment in the absence of the test compound, in which case the test compound is identified as a compound that enhances binding of human c-Maf. In another embodiment, the amount of binding of human c-Maf to the DNA fragment in the presence of the test compound is less than the amount of binding of human c-Maf to the DNA fragment in the absence of the test compound, in which case the test compound is identified as a compound that inhibits binding of human c-Maf.

Yet another aspect of the invention pertains to methods of modulating human c-Maf activity in a cell. The modulatory methods of the invention involve contacting the cell with an agent that modulates human c-Maf activity such that human c-Maf activity in the cell is modulated. The agent may act by modulating the activity of human c-Maf protein in the cell or by modulating transcription of the human c-Maf gene or translation of the human c-Maf mRNA. As used herein, the term "modulating" is intended to include inhibiting or decreasing human c-Maf activity and stimulating or increasing human c-Maf activity. Accordingly, in one embodiment, the agent inhibits human c-Maf activity. In another embodiment, the agent stimulates human c-Maf activity.

A. Inhibitory Agents

According to a modulatory method of the invention, human c-Maf activity is inhibited in a cell by contacting the cell with an inhibitory agent. Inhibitory agents of the invention can be, for example, intracellular binding molecules that act to inhibit the expression or activity of human c-Maf. As used herein, the term "intracellular binding molecule" is intended to include molecules that act intracellularly to inhibit the expression or activity of a protein by binding to the protein itself, to a nucleic acid (e.g., an mRNA molecule) that encodes the protein or to a target with which the protein normally interacts (e.g., to a DNA target sequence to which c-Maf binds). Examples of intracellular binding molecules, described in further detail below, include antisense human c-Maf nucleic acid molecules (e.g., to inhibit translation of human c-Maf mRNA), intracellular anti-human c-Maf antibodies (e.g., to inhibit the activity of human c-Maf protein) and dominant negative mutants of the human c-Maf protein.

In one embodiment, an inhibitory agent of the invention is an antisense nucleic acid molecule that is complementary to a gene encoding human c-Maf or to a portion of said gene, or a recombinant expression vector encoding said antisense nucleic acid molecule. The use of antisense nucleic acids to downregulate the expression of a particular protein in a cell is well known in the art (see e.g., Weintraub, H. et al., Antisense RNA as a molecular tool for genetic analysis, Reviews—*Trends in Genetics*, Vol. 1(1) 1986; Askari, F. K. and McDonnell, W. M. (1996) *N. Eng. J. Med.* 334:316–318; Bennett, M. R. and Schwartz, S. M. (1995) *Circulation* 92:1981–1993; Mercola, D. and Cohen, J. S. (1995) *Cancer Gene Ther.* 2:47–59; Rossi, J. J. (1995) *Br. Med. Bull.* 51:217–225; Wagner, R. W. (1994) *Nature* 372:333–335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA. An antisense nucleic acid for inhibiting the expression of human c-Maf protein in a cell can be designed based upon the nucleotide sequence encoding the human c-Maf protein (e.g., SEQ ID NO: 1 and plasmid pHu-c-Maf), constructed according to the rules of Watson and Crick base pairing.

An antisense nucleic acid can exist in a variety of different forms. For example, the antisense nucleic acid can be an oligonucleotide that is complementary to only a portion of a human c-Maf gene. An antisense oligonucleotides can be constructed using chemical synthesis procedures known in the art. An antisense oligonucleotide can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used. To inhibit human c-Maf expression in cells in culture, one or more antisense oligonucleotides can be added to cells in culture media, typically at about 200 µg oligonucleotide/ml.

Alternatively, an antisense nucleic acid can be produced biologically using an expression vector into which a nucleic acid has been subcloned in an antisense orientation (i e. nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. For example, for inducible expression of antisense RNA, an inducible eukaryotic regulatory system, such as the Tet system (e.g., as described in Gossen, M. and Bujard, H. (1992) *Proc. Natl. Acad. Sci. USA* 89:5547–5551; Gossen, M. et al. (1995) *Science* 268:1766–1769; PCT Publication No. WO 94/29442; and PCT Publication No. WO 96/01313) can be used. The antisense expression vector is prepared as described above for recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector is introduced into cells using a standard transfection technique, as described above for recombinant expression vectors.

In another embodiment, an antisense nucleic acid for use as an inhibitory agent is a ribozyme. Ribozymes are catalytic RNA molecules with ribonuclease activity which are capable of cleaving a single-stranded nucleic acid, such as an mRNA, to which they have a complementary region (for reviews on ribozymes see e.g., Ohkawa, J. et al. (1995) *J. Biochem*. 118:251–258; Sigurdsson, S. T. and Eckstein, F. (1995) *Trends Biotechnol*. 13:286–289; Rossi, J. J. (1995) *Trends Biotechnol*. 13:301–306; Kiehntopf, M. et al. (1995) *J. Mol. Med*. 73:65–71). A ribozyme having specificity for human c-Maf mRNA can be designed based upon the nucleotide sequence of the human c-Maf cDNA. For example, a derivative of a *Tetrahymena* L-19 IVS RNA can be constructed in which the base sequence of the active site is complementary to the base sequence to be cleaved in a human c-Maf mRNA. See for example U.S. Pat. Nos. 4,987,071 and 5,116,742, both by Cech et al. Alternatively, human c-Maf mRNA can be used to select a catalytic RNA having a specific ribonuclease activity from a pool of RNA molecules. See for example Bartel, D. and Szostak, J. W. (1993) *Science* 261: 1411–1418.

Another type of inhibitory agent that can be used to inhibit the expression and/or activity of human c-Maf in a cell is an intracellular antibody specific for the human c-Maf protein. The use of intracellular antibodies to inhibit protein function in a cell is known in the art (see e.g., Carlson, J. R. (1988) *Mol. Cell. Biol.* 8:2638–2646; Biocca, S. et al. (1990) *EMBO J*. 9:101–108; Werge, T. M. et al. (1990) *FEBS Letters* 274:193–198; Carlson, J. R. (1993) *Proc. Natl. Acad. Sci. USA* 90:7427–7428; Marasco, W. A. et al. (1993) *Proc. Natl. Acad. Sci. USA* 90:7889–7893; Biocca, S. et al. (1994) *Bio/Technology* 12:396–399; Chen, S-Y. et al. (1994) *Human Gene Therapy* 5:595–601; Duan, L et al. (1994) *Proc. Natl. Acad. Sci. USA* 91:5075–5079; Chen, S-Y. et al. (1994) *Proc. Natl. Acad. Sci. USA* 91:5932–5936; Beerli, R. R. et al. (1994) *J. Biol. Chem*. 269:23931–23936; Beerli, R. R. et al. (1994) *Biochem. Biophys. Res. Commun*. 204:666–672; Mhashilkar, A. M. et al. (1995) *EMBO J*. 14:1542–1551; Richardson, J. H. et al. (1995) *Proc. Natl. Acad. Sci. USA* 92:3137–3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of human c-Maf activity according to the inhibitory methods of the invention, an intracellular antibody that specifically binds the human c-Maf protein is expressed in the cytoplasm of the cell. To prepare an intracellular antibody expression vector, antibody light and heavy chain cDNAs encoding antibody chains specific for the target protein of interest, e.g., human c-Maf, are isolated, typically from a hybridoma that secretes a monoclonal antibody specific for the human c-Maf protein. Hybridomas secreting anti-human c-Maf monoclonal antibodies, or recombinant anti-human c-Maf monoclonal antibodies, can be prepared as described above. Once a monoclonal antibody specific for human c-Maf protein has been identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91-3242 and in the "Vbase" human germline sequence database.

Once obtained, the antibody light and heavy chain sequences are cloned into a recombinant expression vector using standard methods. To allow for cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., $(Gly_4Ser)_3$) and expressed as a single chain molecule. To inhibit human c-Maf activity in a cell, the expression vector encoding the anti-human c-Maf intracellular antibody is introduced into the cell by standard transfection methods, as discussed hereinbefore.

Yet another form of an inhibitory agent of the invention is an inhibitory form of human c-Maf, also referred to herein as a dominant negative inhibitor. The maf family of proteins are known to homodimerize and to heterodimerize with other AP-1 family members, such as Fos and Jun (see e.g., Kerppola, T. K. and Curran, T. (1994) *Oncogene* 9:675–684; Kataoka, K. et al. (1994) *Mol. Cell. Biol.* 14:700–712). One means to inhibit the activity of transcription factors that form dimers is through the use of a dominant negative inhibitor that has the ability to dimerize with functional transcription factors but that lacks the ability to activate transcription (see e.g., Petrak, D. et al. (1994) *J. Immunol.* 153:2046–2051). By dimerizing with functional transcription factors, such dominant negative inhibitors can inhibit their functional activity. This process may occur naturally as a means to regulate gene expression. For example, there are a number of "small" maf proteins, such as mafK, mafF, mafG and p18, which lack the amino terminal two thirds of c-Maf that contains the transactivating domain (Fujiwara, K. T. et al. (1993) *Oncogene* 8:2371–2380; Igarashi, K. et al. (1995) *J. Biol. Chem.* 270:7615–7624; Andrews, N. C. et al. (1993) *Proc. Natl. Acad. Sci. USA* 90:11488–11492; Kataoka, K. et al. (1995) *Mol. Cell. Biol.* 15:2180–2190). Homodimers of the small maf proteins act as negative regulators of transcription (Igarashi, K. et al. (1994) *Nature* 367:568–572) and three of the small maf proteins (MafK, MafF and MafG) have been shown to competitively inhibit transactivation mediated by the v-Maf oncoprotein (Kataoka, K. et al. (1996) *Oncogene* 12:53–62). Additionally, MafB has been identified as an interaction partner of Ets-1 and shown to inhibit Ets-1-mediated transactivation of the transferrin receptor and to inhibit erythroid differentiation (Sieweke, M. H. et al. (1996) *Cell* 85:49–60).

Accordingly, an inhibitory agent of the invention can be a form of a human c-Maf protein that has the ability to dimerize with other proteins but that lacks the ability to activate transcription. This dominant negative form of a human c-Maf protein may be, for example, a mutated form of human c-Maf in which the transactivation domain has been removed. Such dominant negative human c-Maf proteins can be expressed in cells using a recombinant expression vector encoding the human c-Maf protein, which is introduced into the cell by standard transfection methods. To express a mutant form of human c-Maf lacking a transactivation domain, nucleotide sequences encoding the amino terminal transactivation domain of human c-Maf are removed from the c-maf coding sequences by standard recombinant DNA techniques. Preferably, at least amino acids 1–122 are removed. More preferably, at least amino acids 1–187, or amino acids 1–257, are removed. Nucleotide sequences encoding the basic-leucine zipper region are maintained. The truncated DNA is inserted into a recombinant expression vector, which is then introduced into a cell to allow for expression of the truncated human c-Maf, lacking a transactivation domain, in the cell.

Other inhibitory agents that can be used to inhibit the activity of a human c-Maf protein are chemical compounds that directly inhibit human c-Maf activity or inhibit the interaction between human c-Maf and target DNA or another protein. Such compounds can be identified using screening assays that select for such compounds, as described in detail above.

B. Stimulatory Agents

According to a modulatory method of the invention, human c-Maf activity is stimulated in a cell by contacting the cell with a stimulatory agent. Examples of such stimulatory agents include active human c-Maf protein and nucleic acid molecules encoding human c-Maf that are introduced into the cell to increase human c-Maf activity in the cell. A preferred stimulatory agent is a nucleic acid molecule encoding a human c-Maf protein, wherein the nucleic acid molecule is introduced into the cell in a form suitable for expression of the active human c-Maf protein in the cell. To express a human c-Maf protein in a cell, typically a human c-Maf-encoding DNA is first introduced into a recombinant expression vector using standard molecular biology techniques, as described herein. A human c-Maf-encoding DNA can be obtained, for example, from plasmid pHu-c-Maf or by amplification using the polymerase chain reaction (PCR), using primers based on the human c-Maf nucleotide sequence. Following isolation or amplification of human c-Maf-encoding DNA, the DNA fragment is introduced into an expression vector and transfected into target cells by standard methods, as described herein.

Other stimulatory agents that can be used to stimulate the activity of a human c-Maf protein are chemical compounds that stimulate human c-Maf activity in cells, such as compounds that directly stimulate human c-Maf protein and compounds that promote the interaction between human c-Maf and target DNA or other proteins. Such compounds can be identified using screening assays that select for such compounds, as described in detail above.

The modulatory methods of the invention can be performed in vitro (e.g., by culturing the cell with the agent or by introducing the agent into cells in culture) or, alternatively, in vivo (e.g., by administering the agent to a subject or by introducing the agent into cells of a subject, such as by gene therapy). For practicing the modulatory method in vitro, cells can be obtained from a subject by standard methods and incubated (i.e., cultured) in vitro with a modulatory agent of the invention to modulate human c-Maf activity in the cells. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, monocytes/macrophages can be isolated by adherence on plastic. B cells can be enriched for example, by positive selection using antibodies to B cell surface markers, for example by incubating cells with a specific primary monoclonal antibody (mAb), followed by isolation of cells that bind the mAb using magnetic beads coated with a secondary antibody that binds the primary mAb. Specific cell populations can also be isolated by fluorescence activated cell sorting according to standard methods. If desired, cells treated in vitro with a modulatory agent of the invention can be readministered to the subject. For administration to a subject, it may be preferable to first remove residual agents in the culture from the cells before administering them to the subject. This can be done for example by a Ficoll/Hypaque gradient centrifugation of the cells. For further discussion of ex vivo genetic modification of cells followed by readministration to a subject, see also U.S. Pat. No. 5,399,346 by W. F. Anderson et al.

For practicing the modulatory method in vivo in a subject, the modulatory agent can be administered to the subject such that human c-Maf activity in cells of the subject is modulated. The term "subject" is intended to include living organisms in which an immune response can be elicited. Preferred subjects are mammals. Examples of subjects include humans, monkeys, dogs, cats, mice, rats, cows, horses, goats and sheep.

For stimulatory or inhibitory agents that comprise nucleic acids (including recombinant expression vectors encoding human c-Maf protein, antisense RNA, intracellular antibodies or dominant negative inhibitors), the agents can be introduced into cells of the subject using methods known in the art for introducing nucleic acid (e.g., DNA) into cells in vivo. Examples of such methods encompass both non-viral and viral methods, including:

Direct Injection:

Naked DNA can be introduced into cells in vivo by directly injecting the DNA into the cells (see e.g., Acsadi et al. (1991) *Nature* 332:815–818; Wolff et al. (1990) *Science* 247:1465–1468). For example, a delivery apparatus (e.g., a "gene gun") for injecting DNA into cells in vivo can be used. Such an apparatus is commercially available (e.g., from BioRad).

Cationic Lipids:

Naked DNA can be introduced into cells in vivo by complexing the DNA with cationic lipids or encapsulating the DNA in cationic liposomes. Examples of suitable cationic lipid formulations include N-[-1-(2,3-dioleoyloxy)propyl]N,N,N-triethylammonium chloride (DOTMA) and a 1:1 molar ratio of 1,2-dimyristyloxy-propyl-3-dimethylhydroxyethylammonium bromide (DMRIE) and dioleoyl phosphatidylethanolamine (DOPE) (see e.g., Logan, J. J. et al. (1995) *Gene Therapy* 2:38–49; San, H. et al. (1993) *Human Gene Therapy* 4:781–788).

Receptor-Mediated DNA Uptake:

Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122–2126).

Retroviruses:

Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψ Crip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses:

The genome of an adenovirus can be manipulated such that it encodes and expresses a gene product of interest but is inactivated in terms of its ability to replicate in a normal lytic viral life cycle. See for example Berkner et al (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-associated Viruses:

Adeno-associated virus (AAV) is a naturally occurring defective virus that requires another virus, such as an adenovirus or a herpes virus, as a helper virus for efficient replication and a productive life cycle. (For a review see Muzyczka et al *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product.

In a preferred embodiment, a retroviral expression vector encoding human c-Maf is used to express human c-Maf protein in cells in vivo, to thereby stimulate c-Maf protein activity in vivo. Such retroviral vectors can be prepared according to standard methods known in the art (discussed further above).

A modulatory agent, such as a chemical compound, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described above in subsection IV.

The identification of c-Maf as a key regulator of the production of IL-4 (see e.g., PCT Publication WO 97/39721 and Ho, I-C. et al. (1996) *Cell* 85:973–983), and hence continued formation of Th2 cells, allows for selective manipulation of T cell subsets in a variety of clinical situations using the modulatory methods of the invention. The stimulatory methods of the invention (i.e., methods that use a stimulatory agent to enhance human c-Maf activity) result in production of Th2-associated cytokines, with concomitant promotion of a Th2 response and downregulation of a Th1 response. In contrast, the inhibitory methods of the invention (i.e., methods that use an inhibitory agent to downmodulate human c-Maf activity) inhibit the production of Th2-associated cytokines, with concomitant downregulation of a Th2 response and promotion of a Th1 response. Thus, to treat a disease condition wherein a Th2 response is beneficial, a stimulatory method of the invention is selected such that Th2 responses are promoted while downregulating Th1 responses. Alternatively, to treat a disease condition wherein a Th1 response is beneficial, an inhibitory method of the invention is selected such that Th2 responses are downregulated while promoting Th1 responses. Application of the methods of the invention to the treatment of disease conditions may result in cure of the condition, a decrease in the type or number of symptoms associated with the condition, either in the long term or short term (i.e., amelioration of the condition) or simply a transient beneficial effect to the subject.

Numerous disease conditions associated with a predominant Th1 or Th2-type response have been identified and could benefit from modulation of the type of response mounted in the individual suffering from the disease condition. Application of the immunomodulatory methods of the invention to such diseases is described in further detail below.

A. Allergies

Allergies are mediated through IgE antibodies whose production is regulated by the activity of Th2 cells and the cytokines produced thereby. In allergic reactions, IL-4 is produced by Th2 cells, which further stimulates production of IgE antibodies and activation of cells that mediate allergic reactions, i.e., mast cells and basophils. IL-4 also plays an important role in eosinophil mediated inflammatory reactions. Accordingly, the inhibitory methods of the invention can be used to inhibit the production of Th2-associated cytokines, and in particular IL-4, in allergic patients as a means to downregulate production of pathogenic IgE antibodies. An inhibitory agent may be directly administered to the subject or cells (e.g., Thp cells or Th2 cells) may be obtained from the subject, contacted with an inhibitory agent ex vivo, and readministered to the subject. Moreover, in certain situations it may be beneficial to coadminister to the subject the allergen together with the inhibitory agent or cells treated with the inhibitory agent to inhibit (e.g. desensitize) the allergen-specific response. The treatment may be further enhanced by administering other Th1-promoting agents, such as the cytokine IL-12 or antibodies to Th2-associated cytokines (e.g., anti-IL-4 antibodies), to the allergic subject in amounts sufficient to further stimulate a Th1-type response.

B. Cancer

The expression of Th2-promoting cytokines has been reported to be elevated in cancer patients (see e.g., Yamamura, M., et al. (1993) *J. Clin. Invest.* 91:1005–1010; Pisa, P., et al. (1992) *Proc. Natl. Acad. Sci. USA* 89:7708–7712) and malignant disease is often associated with a shift from Th1 type responses to Th2 type responses along with a worsening of the course of the disease. Accordingly, the inhibitory methods of the invention can be used to inhibit the production of Th2-associated cytokines in cancer patients, as a means to counteract the Th1 to Th2 shift and thereby promote an ongoing Th1 response in the patients to ameliorate the course of the disease. The inhibitory method can involve either direct administration of an inhibitory agent to a subject with cancer or ex vivo treatment of cells obtained from the subject (e.g., Thp or Th2 cells) with an inhibitory agent followed by readministration of the cells to the subject. The treatment may be further enhanced by administering other Th1-promoting agents, such as the cytokine IL-12 or antibodies to Th2-associated cytokines (e.g., anti-IL-4 antibodies), to the recipient in amounts sufficient to further stimulate a Th1-type response.

C. Infectious Diseases

The expression of Th2-promoting cytokines also has been reported to increase during a variety of infectious diseases, including HIV infection, tuberculosis, leishmaniasis, schistosomiasis, filarial nematode infection and intestinal nematode infection (see e.g.; Shearer, G. M. and Clerici, M. (1992) *Prog. Chem. Immunol.* 54:21–43; Clerici, M and Shearer, G. M. (1993) *Immunology Today* 14:107–111; Fauci, A. S. (1988) *Science* 239:617–623; Locksley, R. M. and Scott, P. (1992) *Immunoparasitology Today* 1:A58–A61; Pearce, E. J., et al. (1991) *J. Exp. Med.* 173:159–166; Grzych, J-M., et al. (1991) *J. Immunol.* 141:1322–1327; Kullberg, M. C., et al. (1992) *J. Immunol.* 148:3264–3270; Bancroft, A. J., et al. (1993) *J. Immunol.* 150: 1395–1402; Pearlman, E., et al. (1993) *Infect. Immun.* 61:1105–1112; Else, K. J., et al. (1994) *J. Exp. Med.* 179:347–351) and such infectious diseases are also associated with a Th1 to Th2 shift in the immune response. Accordingly, the inhibitory methods of the invention can be used to inhibit the production of Th2-associated cytokines in subjects with infectious diseases, as a means to counteract the Th1 to Th2 shift and thereby promote an ongoing Th1 response in the patients to ameliorate the course of the infection. The inhibitory method can involve either direct administration of an inhibitory agent to a subject with an infectious disease or ex vivo treatment of cells obtained from the subject (e.g., Thp or Th2 cells) with an inhibitory agent followed by readministration of the cells to the subject. The treatment may be further enhanced by administering other Th1-promoting agents, such as the cytokine IL-12 or antibodies to Th2-associated cytokines (e.g., anti-IL-4 antibodies), to the recipient in amounts sufficient to further stimulate a Th1-type response.

D. Autoimmune Diseases

The stimulatory methods of the invention can be used therapeutically in the treatment of autoimmune diseases that are associated with a Th2-type dysfunction. Many autoimmune disorders are the result of inappropriate activation of T cells that are reactive against self tissue and that promote the production of cytokines and autoantibodies involved in the pathology of the diseases. Modulation of T helper-type responses can have an effect on the course of the autoimmune disease. For example, in experimental allergic encephalomyelitis (EAE), stimulation of a Th2-type response by administration of IL-4 at the time of the induction of the disease diminishes the intensity of the autoimmune disease (Paul, W. E., et al. (1994) *Cell* 76:241–251). Furthermore, recovery of the animals from the disease has been shown to be associated with an increase in a Th2-type response as evidenced by an increase of Th2-specific cytokines (Koury, S. J., et al. (1992) *J. Exp. Med.* 176:1355–1364). Moreover, T cells that can suppress EAE secrete Th2-specific cytokines (Chen, C., et al. (1994) *Immunity* 1:147–154). Since stimulation of a Th2-type response in EAE has a protective effect against the disease, stimulation of a Th2 response in subjects with multiple sclerosis (for which EAE is a model) is likely to be beneficial therapeutically.

Similarly, stimulation of a Th2-type response in type I diabetes in mice provides a protective effect against the disease. Indeed, treatment of NOD mice with IL-4 (which promotes a Th2 response) prevents or delays onset of type I diabetes that normally develops in these mice (Rapoport, M. J., et al. (1993) *J. Exp. Med.* 178:87–99). Thus, stimulation of a Th2 response in a subject suffering from or susceptible to diabetes may ameliorate the effects of the disease or inhibit the onset of the disease.

Yet another autoimmune disease in which stimulation of a Th2-type response may be beneficial is rheumatoid arthritis (RA). Studies have shown that patients with rheumatoid arthritis have predominantly Th1 cells in synovial tissue (Simon, A. K., et al., (1994) *Proc. Natl. Acad. Sci. USA* 91:8562–8566). By stimulating a Th2 response in a subject with RA, the detrimental Th1 response can be concomitantly downmodulated to thereby ameliorate the effects of the disease.

Accordingly, the stimulatory methods of the invention can be used to stimulate production of Th2-associated cytokines in subjects suffering from, or susceptible to, an autoimmune disease in which a Th2-type response is beneficial to the course of the disease. The stimulatory method can involve either direct administration of a stimulatory agent to the subject or ex vivo treatment of cells obtained from the subject (e.g., Thp, Th1 cells, B cells, non-lymphoid cells) with a stimulatory agent followed by readministration of the cells to the subject. The treatment may be further enhanced by administering other Th2-promoting agents, such as IL-4 itself or antibodies to Th1-associated cytokines, to the subject in amounts sufficient to further stimulate a Th2-type response.

In contrast to the autoimmune diseases described above in which a Th2 response is desirable, other autoimmune diseases may be ameliorated by a Th1-type response. Such diseases can be treated using an inhibitory agent of the invention (as described above for cancer and infectious diseases). The treatment may be further enhanced by administrating a Th1-promoting cytokine (e.g., IFN-γ) to the subject in amounts sufficient to further stimulate a Th 1-type response.

The efficacy of agents for treating autoimmune diseases can be tested in the above described animal models of human diseases (e.g., EAE as a model of multiple sclerosis and the NOD mice as a model for diabetes) or other well characterized animal models of human autoimmune diseases. Such animal models include the mrl/lpr/lpr mouse as a model for lupus erythematosus, murine collagen-induced arthritis as a model for rheumatoid arthritis, and murine experimental myasthenia gravis (see Paul ed., *Fundamental Immunology*, Raven Press, New York, 1989, pp. 840–856). A modulatory (i.e., stimulatory or inhibitory) agent of the invention is administered to test animals and the course of the disease in the test animals is then monitored by the standard methods for the particular model being used. Effectiveness of the modulatory agent is evidenced by amelioration of the disease condition in animals treated with the agent as compared to untreated animals (or animals treated with a control agent).

Non-limiting examples of autoimmune diseases and disorders having an autoimmune component that may be treated according to the invention include diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

E. Transplantation

While graft rejection or graft acceptance may not be attributable exclusively to the action of a particular T cell subset (i.e., Th1 or Th2 cells) in the graft recipient (for a discussion see Dallman, M. J. (1995) Curr. Opin. Immunol. 7:632–638), numerous studies have implicated a predominant Th2 response in prolonged graft survival or a predominant Th2 response in graft rejection. For example, graft acceptance has been associated with production of a Th2 cytokine pattern and/or graft rejection has been associated with production of a Th1 cytokine pattern (see e.g., Takeuchi, T. et al. (1992) Transplantation 53:1281–1291; Tzakis, A. G. et al. (1994) J. Pediatr. Surg. 29:754–756; Thai, N. L. et al. (1995) Transplantation 59:274–281). Additionally, adoptive transfer of cells having a Th2 cytokine phenotype prolongs skin graft survival (Maeda, H. et al. (1994) Int. Immunol. 6:855–862) and reduces graft-versus-host disease (Fowler, D. H. et al. (1994) Blood 84:3540–3549; Fowler, D. H. et al. (1994) Prog. Clin. Biol. Res. 389:533–540). Still further, administration of IL-4, which promotes Th2 differentiation, prolongs cardiac allograft survival (Levy, A. E. and Alexander, J. W. (1995) Transplantation 60:405–406), whereas administration of IL-12 in combination with anti-IL-10 antibodies, which promotes Th1 differentiation, enhances skin allograft rejection (Gorczynski, R. M. et al. (1995) Transplantation 60:1337–1341).

Accordingly, the stimulatory methods of the invention can be used to stimulate production of Th2-associated cytokines in transplant recipients to prolong survival of the graft. The stimulatory methods can be used both in solid organ transplantation and in bone marrow transplantation (e.g., to inhibit graft-versus-host disease). The stimulatory method can involve either direct administration of a stimulatory agent to the transplant recipient or ex vivo treatment of cells obtained from the subject (e.g., Thp, Th1 cells, B cells, non-lymphoid cells) with a stimulatory agent followed by readministration of the cells to the subject. The treatment may be further enhanced by administering other Th2-promoting agents, such as IL-4 itself or antibodies to Th1-associated cytokines, to the recipient in amounts sufficient to further stimulate a Th2-type response.

In addition to the foregoing disease situations, the modulatory methods of the invention also are useful for other purposes. For example, the stimulatory methods of the invention (i.e., methods using a stimulatory agent) can be used to stimulate production of Th2-promoting cytokines (e.g., IL-4) in vitro for commercial production of these cytokines (e.g., cells can be contacted with the stimulatory agent in vitro to stimulate IL-4 production and the IL-4 can be recovered from the culture supernatant, further purified if necessary, and packaged for commercial use).

Furthermore, the modulatory methods of the invention can be applied to vaccinations to promote either a Th1 or a Th2 response to an antigen of interest in a subject. That is, the agents of the invention can serve as adjuvants to direct an immune response to a vaccine either to a Th1 response or a Th2 response. For example, to stimulate an antibody response to an antigen of interest (i.e., for vaccination purposes), the antigen and a stimulatory agent of the invention can be coadministered to a subject to promote a Th2 response to the antigen in the subject, since Th2 responses provide efficient B cell help and promote IgG1 production. Alternatively, to promote a cellular immune response to an antigen of interest, the antigen and an inhibitory agent of the invention can be coadministered to a subject to promote a Th1 response to the antigen in a subject, since Th1 responses favor the development of cell-mediated immune responses (e.g., delayed hypersensitivity responses). The antigen of interest and the modulatory agent can be formulated together into a single pharmaceutical composition or in separate compositions. In a preferred embodiment, the antigen of interest and the modulatory agent are administered simultaneously to the subject. Alternatively, in certain situations it may be desirable to administer the antigen first and then the modulatory agent or vice versa (for example, in the case of an antigen that naturally evokes a Th1 response, it may be beneficial to first administer the antigen alone to stimulate a Th1 response and then administer a stimulatory agent, alone or together with a boost of antigen, to shift the immune response to a Th2 response).

This invention is further illustrated by the following example, which should not be construed as limiting. The contents of all references, patents and published patent applications cited throughout this application are hereby incorporated by reference. Additionally, all nucleotide and amino acid sequences deposited in public databases referred to herein are also hereby incorporated by reference.

EXAMPLE

Isolation and Characterization of a Human c-Maf Nucleic Acid

To isolate a nucleic acid molecule encoding human c-maf, a human genomic DNA library in lambda phage (commercially available from Stratagene) was screened with a radiolabeled DNA probe derived from the 3' untranslated region of the mouse c-Maf gene. Following hybridization under standard conditions, filters were washed under stringent conditions in 0.2×SSC, 0.1% SDS wash buffer at approximately 62° C. Phage clones that remained hybridized to the probe under these conditions were selected and isolated to purity. The genomic inserts of the isolated phage were subcloned into the plasmid vector pBluescript KS/II, by restriction digestion of the phage DNA with NheI and insertion into the XbaI site of the plasmid. E. coli bacterial cells carrying a pBluescript plasmid containing the human c-Maf coding region, referred to herein as pHu-c-Maf, has been deposited under the provisions of the Budapest Treaty with the American Type Culture Collection, Rockville, Md., on Feb. 24, 1998 and assigned ATCC Accession No. 98671. This plasmid contains an NheI fragment of approximately 4.2 kb (derived from the isolated phage), cloned into the compatible XbaI site of the plasmid vector, to thereby create a ~4.2 kb NheI/XbaI insert that encodes human c-Maf. It should be noted that upon ligation of the NheI fragment into the XbaI site, these restriction sites are not regenerated and, thus, to excise the fragment from the plasmid, it is necessary to use adjacent restriction sites within the pBluescript polylinker.

The coding region of human c-Maf, contained in the pHu-c-Maf plasmid, was sequenced by standard dideoxy sequencing methods. The nucleotide and predicted amino acid sequences are shown in SEQ ID NOs: 1 and 2, respectively.

The coding region encompasses approximately 1.2 kb of DNA and thus, the remainder of the 4.2 kb insert of pHu-c-Maf represents 5' and 3' untranslated sequences. FIG. 1 shows a comparison of the nucleotide sequence of hu-c-Maf shown of SEQ ID NO: 1 with the mouse c-Maf coding region. A number of nucleotide differences between the two coding regions are evident, which differences are boxed in FIG. 1. FIG. 2 shows a comparison of the amino acid sequence of hu-c-Maf shown of SEQ ID NO: 2 with the mouse c-Maf amino acid sequence. Again, a number of amino acid differences between the two proteins are evident, which differences are boxed in FIG. 2. The overall structure of the human c-Maf protein, however, is conserved with the mouse c-Maf protein, including the presence of a leucine zipper domain at amino acid positions 313–348 of SEQ ID NO: 2.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for identifying a compound that modulates the activity of a human c-Maf protein, comprising providing an indicator cell that comprises a recombinant expression vector encoding a human c-Maf protein of SEQ ID NO.:2, wherein the human c-Maf-coding sequences are operatively linked to regulatory sequences that allow for constitutive expression of human c-Maf in the indicator cell, and a reporter gene responsive to the human c-Maf protein;

contacting the indicator composition with a test compound; and determining the effect of the test compound on the activity of the human c-Maf protein in the indicator cell wherein the step of determining comprises evaluating the expression of the reporter gene in the presence and absence of the test compound, to thereby identify a compound that modulates the activity of a human c-Maf protein.

2. The method of claim 1, wherein the reporter gene comprises nucleotides −157 to +58 relative to the +1 start site of transcription of the interleukin-4 gene.

3. The method of claim 1, wherein the reporter gene comprises about 3 kb of upstream regulatory sequences of the interleukin-4 gene.

4. The method of claim 1, wherein the reporter gene is selected from the group consisting of genes that encode: chloramphenicol acetyltransferase, beta-galactosidase, alkaline phosphatase and luciferase.

5. The method of claim 1, wherein the indicator cell does not normally express human c-Maf.

6. The method of claim 1, wherein the indicator cell is a B cell.

7. The method of claim 6, wherein the indicator cell is a M12 B lymphoma cell.

8. The method of claim 1, wherein the indicator cell is a Th1 cell clone.

9. The method of claim 8, wherein the indicator cell is an AE7 cells.

10. The method of claim 1, wherein the indicator cell is a nonlymphoid cell.

11. The method of claim 10, wherein the indicator cell is a HEPG2 hepatoma cell.

12. The method of claim 10, wherein the indicator cell is a yeast cell.

13. A method for identifying a compound that modulates an immune response, comprising
providing an indicator cell that comprises a recombinant expression vector encoding a human c-Maf protein of SEQ ID NO.:2, wherein the human c-Maf-coding sequences are operatively linked to regulatory sequences that allow for constitutive expression of human c-Maf in the indicator cell, and a Th2-associated cytokine gene responsive to the human c-Maf protein;
contacting the indicator composition with a test compound; and
determining the effect of the test compound on an immune response, wherein the step of determining comprises evaluating the effect of the compound on expression of the Th2-associated cytokine gene in the presence and the absence of the test compound, to thereby identify a compound that modulates an immune response.

14. The method of claim 13, wherein the effect of the test compound on an immune response is determined by determining the effect of the compound on production of a Th2-associated cytokine protein.

15. The method of claim 14, wherein the Th2-associated cytokine gene is an interleukin-4 gene.

16. The method of claim 13, wherein the effect of the test compound on the expression of a Th2-associated cytokine gene is determined by determining the effect of the compound on the development of T helper type 1 (Th1) cells.

17. The method of claim 13, wherein the effect of the test compound on the expression of a Th2-associated cytokine gene is determined by determining the effect of the compound on the development of T helper type 2 (Th2) cells.

18. The method of claim 1, wherein the reporter gene is a Th2-associated cytokine.

19. The method of claim 13 or 18, wherein the Th2-associated cytokine is interleukin-4.

20. The method of claim 1 or 13, wherein the reporter gene is operatively linked to regulatory sequences of a Th2-associated cytokine gene.

21. The method of claim 1 or 13, wherein the human c-Maf coding sequences are operatively linked to regulatory sequences of the endogenous human c-Maf gene, wherein the regulatory sequences of the endogenous human c-Maf gene comprise the untranslated sequences of the NheI/XbaI fragment of pHu-c-Maf (ATCC Accession No. 98671).

22. A method for identifying a compound that modulates the activity of a human c-Maf protein comprising,
providing an indicator cell comprising a recombinant expression vector encoding a human c-Maf protein comprising the NheI/XbaI fragment of pHu-c-Maf (ATCC Accession No. 98671), wherein the human c-Maf-coding sequences are operatively linked to regulatory sequences that allow for constitutive expression of human c-Maf in the indicator cell, and a cytokine gene responsive to the human c-Maf protein,
contacting the indicator cell with a test compound, and
determining the effect of the test compound on human c-Maf activity by evaluating the level of cytokine production in the indicator cell in the presence and absence of the test compound, wherein a modulation of the level of cytokine production identifies the test compound as a modulator of the activity of a human c-Maf protein.

23. The method of claim 22, wherein the level of cytokine production is determined by detecting cytokine mRNA in the indicator cell.

24. The method of claim 22, wherein the level of cytokine production is determined by detecting cytokine secretion into the culture supernatant.

25. The method of claim 22, wherein the cytokine is interleukin-4.

* * * * *